(12) United States Patent
Bierbach et al.

(10) Patent No.: US 10,047,057 B2
(45) Date of Patent: Aug. 14, 2018

(54) FUNCTIONALIZED TYROSINE KINASE INHIBITORS MODIFIED WITH PRECIOUS METAL ELECTROPHILES AND METHODS ASSOCIATED THEREWITH

(71) Applicant: WAKE FOREST UNIVERSITY, Winston-Salem, NC (US)

(72) Inventors: Ulrich Bierbach, Winston-Salem, NC (US); Mu Yang, Winston-Salem, NC (US); Amanda J Pickard, New York, NY (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 15/126,443

(22) PCT Filed: Mar. 15, 2015

(86) PCT No.: PCT/US2015/020634
§ 371 (c)(1),
(2) Date: Sep. 15, 2016

(87) PCT Pub. No.: WO2015/142683
PCT Pub. Date: Sep. 24, 2015

(65) Prior Publication Data
US 2017/0081293 A1    Mar. 23, 2017

Related U.S. Application Data

(60) Provisional application No. 61/953,761, filed on Mar. 15, 2014.

(51) Int. Cl.
*C07D 239/94* (2006.01)
*C07F 15/00* (2006.01)
*C07F 1/00* (2006.01)

(52) U.S. Cl.
CPC ............ *C07D 239/94* (2013.01); *C07F 1/005* (2013.01); *C07F 15/0093* (2013.01)

(58) Field of Classification Search
CPC .................................................. C07D 239/94
See application file for complete search history.

(56) References Cited

U.S. PATENT DOCUMENTS

2008/0194596 A1    8/2008    Letrent
2009/0018131 A1    1/2009    Adams et al.
2013/0225811 A1    8/2013    Wang et al.

OTHER PUBLICATIONS

Pinedo et al. (2000).*
McMahon et al (2000).*
Modjtahedi et al., "Epidermal growth factor receptor inhibitors in cancer treatment: advances, challenges and opportunities," Anti-Cancer Drugs (2009); 20(10):851-855.
Wheler et al., "Revisiting Clinical Trials Using EGFR Inhibitor-Based Regiments in Patients with Advanced Non-Small Cell Lung Cancer: A Retrospective Analysis of an MD Anderson Cancer Center Phase I Population," Oncotarget (May 2013); 4(5):772-784.
Townsley et al., "Phase II study of erlotinib (OSI=774) in patients with metastatic colorectal cancer," British Journal of Cancer (2006); 94:1136-1143.
Taylor et al., "Targeting EGFR for Treatment of Glioblastoma: Molecular Basis to Overcome Resistance," Curr Cancer Drug Targets (Mar. 2012); 12(3):197-209.
Kelley et al., "Erlotinib in the treatment of advanced pancreatic cancer," Biologics: Targets & Therapy (2008); 2(1):83-95.
Quesnelle et al., "Preclinical modeling of EGFR inhibitor resistance in head and neck cancer," Cancer Biology & Therapy (Aug. 2012); 13(10):935-945.

* cited by examiner

*Primary Examiner* — Paul V Ward
(74) *Attorney, Agent, or Firm* — Fox Rothschild LLP

(57) ABSTRACT

Newly synthesized thiourea-modified 3-chloro-4-fluoroanilino-quinazoline derivatives have been studied as terminal carrier ligands in linear gold(I) complexes. The molecules mimic the tyrosine kinase inhibitor gefitinib (by computational docking experiments). Thiourea groups were either directly attached to quinazoline-C6 or linked to this position via a flexible ethylamino chain. One compound tested acts as a thiourea-S/quinazoline-N1 mixed-donor ligand, giving an unusual dinuclear complex as determined by X-ray crystallography and/or electrospray mass spectrometry. One compound formed the desired stable linear complex. The biological activity of the carrier ligands and corresponding gold(I) complexes was studied in NCI-H460 and NCI-H1975 lung cancer cells. One compound that was tested partially overcomes resistance to gefitinib in NCI-H1975 (with $IC_{50}$ values of 1.7 and 30 μM, respectively), and the corresponding gold complex (13) maintains activity in the low-micromolar concentration range.

22 Claims, 2 Drawing Sheets a)

b)

FUNCTIONALIZED TYROSINE KINASE INHIBITORS MODIFIED WITH PRECIOUS METAL ELECTROPHILES AND METHODS ASSOCIATED THEREWITH

The present invention claims priority under 35 USC 119(e) to U.S. Provisional Application No. 61/953,761 filed Mar. 15, 2014, the entire contents of which is incorporated by reference in its entirety.

FIELD OF THE INVENTION

The present invention relates to thiourea/amidine functionalized tyrosine kinase inhibitors modified with gold, platinum, and other precious metal compounds. The thiourea/amidine-modified 3-chloro-4-fluoroanilino-quinazoline derivatives were studied as carrier ligands in linear gold(I) or square planar platinum(II) complexes. The molecules mimic the tyrosine kinase inhibitor gefitinib (by computational docking experiments). Thiourea or amidine groups were either directly attached to quinazoline-C6 or linked to this position via a flexible alkylamino chain. The approach allows the selective targeting of clinically relevant tyrosine kinases with classical anticancer metals as a means of overcoming drug resistance in intractable cancer. The metals introduced may act as electrophiles and form bonds with amino acid residues in the kinases' active sites, such as cysteine, methionine, histidine, and lysine.

BACKGROUND OF THE INVENTION

Mutationally activated tyrosine kinases (TK) of the epidermal growth factor receptor (EGFR) family are considered a major driver of cancer cell survival and aggressive tumor growth. In non-small cell lung cancer, expression levels of EGFR are inversely correlated with survival of the disease. Somatic (activating) EGFR mutations sensitize cancer cells to small-molecule tyrosine kinase inhibitors (TKIs), which target the enzyme's ATP binding site and show potent antiproliferative properties. Gefitinib is a quinazoline-based TKI indicated against cancers harboring aberrant EGFR, in particular lung carcinomas. Unfortunately, the efficacy of this drug is limited by the emergence of acquired resistance as a consequence of a secondary mutation within the ATP binding pocket. One currently pursued approach to combatting this form of resistance observed for mutant EGFR and other clinically relevant kinases is to turn the reversible TKIs into irreversible inhibitors (ITKIs). These molecules contain a strategically positioned reactive electrophilic group (usually a Michael acceptor), which is able to form a covalent bond with accessible cysteine residues in the active sites of the targetable enzymes.

BRIEF SUMMARY OF THE INVENTION

In an embodiment, the present invention relates to introducing a gold(I) or platinum(II) based electrophile into a TKI structure that can be targeted to the solvent-accessible cysteine-797 near the entrance to the ATP binding pocket of EGFR-TK. These pharmacophores would combine the high sulfur affinity of gold(I) or platinum(II) with the selectivity and nanomolar binding affinity of an EGFR-TK-targeted ligand. The use of gold(I) or platinum(II) as electrophilic moieties in the proposed structures in place of the Michael acceptor was inspired by the mechanisms of action of gold(I) drugs, which react with (seleno)cysteine residues in proteolytic and redox-active enzymes and the reactivity of platinum drugs with cysteine containing species demonstrated in the inventors' previous research. While these interactions are generally unselective, targeting of specific cysteine residues by gold(I) and platinum(II) complexes containing target-selective carriers may occur.

Thus, in an embodiment, the present invention relates to introducing a precious metal electrophile into a TKI structure that can be targeted to the solvent-accessible cysteine-797 near the entrance to the ATP binding pocket of EGFR-TK. The desired pharmacophore combines the high sulfur affinity of gold(I) and platinum(II) with the selectivity and nanomolar binding affinity of an EGFR-TK-targeted ligand.

In an embodiment, the present invention relates to novel thiourea and amidine-modified TKIs derived from a quinazoline scaffold. The present invention also relates to the ability of novel functionalized TKIs to serve as potential carrier ligands in (pseudo)halide and phosphine substituted gold(I) and mixed-ligand platinum(II) complexes. At least one TKI derivative was identified that partially overcomes resistance to gefitinib in NSCLC cell lines harboring wild-type and mutated EGFR kinase domains. Additionally, two platinum(II) derivatives, P3-T2 and P9-T2, displayed low nanomolar binding affinities to wild-type EGFR, similar to gefitinib Accordingly, in an embodiment, the present invention relates to generating unique types of hybrid pharmacophores, which lend themselves to modular high-throughput screening and extended structure-activity relationship studies. Libraries can be assembled using simple ligand substitution chemistry (see for example Scheme 1) and metal-facilitated amine-to-nitrile addition chemistry (see for example Schemes 4-6).

In an embodiment, although the relatively high $IC_{50}$ of one derivative can be explained by its aqueous reactivity, which leads to an undesired, deactivating auto-chelation, which does not allow for nucleophile binding and possibly prevents receptor binding, other compounds of the present invention have lower $IC_{50}$ values. The prototypes P3-T3 and P3-T4 are expected to have lower $IC_{50}$ values. In one variation, the chemical strategy used to generate these unique types of hybrid pharmacophores lend themselves to modular screening and extended structure-activity relationship studies.

Thus, the compounds, compositions and methods of the present invention are likely to add to the useful platinum-based drugs that are currently being used worldwide against genitourinary (bladder, ovaries, testes) cancers and carcinomas of the head and neck, as well as colon cancers. The present compounds, compositions and methods show an altered spectrum of activity compared to the currently available drugs and show excellent activity in cancers insensitive to the available clinical platinums, as well as the traditional kinase inhibitors.

DETAILED DESCRIPTION OF THE INVENTION

Figure 1:
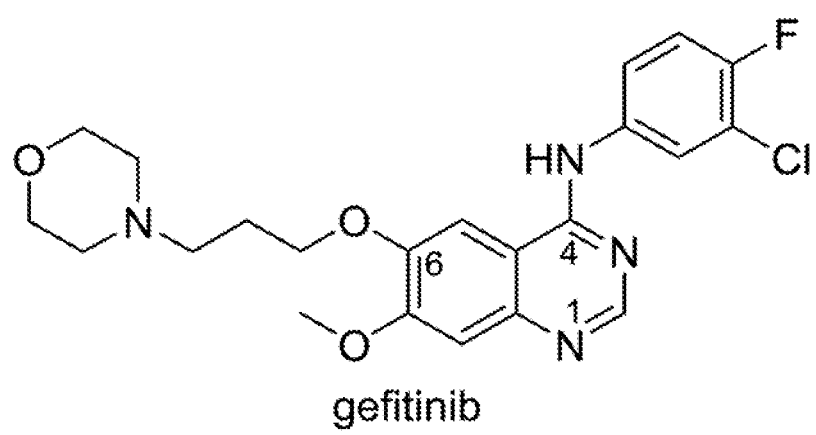
FIG. 1 shows the structure of gefitinib

In an embodiment, the present invention relates to a new class of chemotherapy compositions, compounds and methods aimed towards treating cancer caused by the overexpression and/or mutation of the epidermal growth factor receptor (EGFR), specifically non-small cell lung cancer (NSCLC). In an embodiment, the present invention relates to synthetic routes capable of utilizing EGFR tyrosine kinase inhibitors (TKIs) as scaffolds for precious metal conjugation, leading to irreversible inhibition of wildtype and mutant EGFR in cancerous models via a solvent-accessible reactive cysteine residue in the ATP-binding pocket of the enzyme. The chemical compositions of these metal-TKI hybrid agents are distinct from those of current reversible and irreversible TKIs currently in the clinic and on the market. These new metal-TKI hybrid agents (e.g., gold and platinum) possess the ability to result in decreased systemic toxicity when compared to classical DNA-targeted metal-based chemotherapy (e.g. cisplatin) by driving the new agents towards proteins involved in cancer proliferation and survival rather than towards genomic DNA.

Thus, in an embodiment, the present invention may be useful for first- and/or second-line treatment option for cancers that are inherently resistant, or, have become resistant to clinical therapies, especially classical platinum drugs. The present invention may meet the urgent need that exists for mechanistically novel drugs for the life-prolonging/curative treatment of NSCLC.

Thus, in an embodiment, the present invention relates to new gold(I) and platinum(II)-TKI hybrid agents capable of utilizing the inherent nanomolar binding affinity of the TKI to create metal-induced irreversible enzyme inhibition, which was only previously available via Michael acceptor/donor interactions.

In an embodiment, the present invention also relates to synthetic methodologies capable of producing precious metal-TKI hybrid agents that are able to irreversibly inhibit a wide array of structurally diverse tyrosine kinases with solvent-accessible cysteine or methionine residues in the ATP binding pocket with great specificity.

Moreover, in an embodiment, the present invention relates to the design and synthesis of structurally new and previously undisclosed gold(I) and platinum(II)-TKI compounds/compositions displaying promising kinase selectivity and biological activity when compared to FDA-approved and widely used gefitinib.

In a variation, the present invention also relates to new thiourea-containing kinase inhibitors (T1) that are capable of overcoming the intrinsic resistance caused by the secondary T790M EGFR mutation to classical TKIs (gefitinib).

In an embodiment, the present compounds/compositions containing P3-T2 and/or P9-T2 show wildtype EGFR dissociation constants comparable to gefitinib.

In an embodiment, the present invention relates to a new use for anti-cancer metals, allowing them to be repurposed for selective molecularly targeted therapies for the management of resistant forms of cancer.

In an embodiment, the present invention relates to a new, selective target for platinum-based chemotherapy.

In an embodiment, the present invention uses the platinum and gold-based compounds to target several kinases for cancer chemotherapy, including the ErbB family of enzymes, VEGFR, and FGFR, among others. Small molecule kinase inhibitors often lose their effectiveness in tumors over time as a consequence of secondary mutations that significantly decrease the drug-enzyme binding affinity. The present invention attempts to overcome this type of acquired tumor resistance by introducing irreversible inhibitors that covalently attach to the ATP binding pocket. The compounds/compositions and methods will serve as kinase inhibitors containing cysteine-binding metal-based electrophiles. The compounds feature organic ATP-mimicking scaffolds that bind to the target kinase active site with high affinity and selectivity while the electrophilic metal induces a permanent coordinative bond with the amino acid residue to achieve irreversible inhibition. Accordingly, in one embodiment, the present invention presents structure-guided design and synthesis of these classes of molecules.

Several of the synthesized target molecules showed binding constants ($K_d$) in the low-nanomolar range in competition binding assays and high selectivity for the targeted kinase domain in a panel of 145 wild-type and clinically relevant mutated kinases (KinomeScan, DiscoverX, Fremont, Calif.). The ability of the electrophilic agents to induce irreversible adducts was studied by LC ESI-MS/MS in pepsin digests of kinase incubated with inhibitor. Moreover, the in vitro cytotoxicity of selected derivatives was studied in solid tumor cell lines. The data generated suggest that the new pharmacophores will likely have applications as therapeutics capable of overcoming acquired tumor resistance by irreversibly inhibiting deregulated kinases.

To generate a gold-modified TKI, an N-heterocyclic quinazoline scaffold was used and the N-(3-chloro-4-fluorophenyl) group from gefitinib (FIG. 1), which target the adenine binding site and an adjacent hydrophobic pocket of EGFR-TK, respectively. The 6-position of the quinazoline C6 ring was chosen as attachment point for a side chain carrying a cysteine-affinic gold(I) moiety, similar in design to relevant Michael acceptor-based ITKIs. The goal of this design was to favor binding of the metal with cysteine-797 proximal to the kinase's catalytic cleft without compromising the ligand's interactions with the binding pocket. The linkage between the electrophile and the TKI may be achieved via formation of a strong Au(I)—S bond with a thiourea residue, a thiol-like donor group previously explored in biologically relevant carrier ligands of this metal.

A docking study was performed to examine the conformational space and receptor binding of thiourea-modified TKIs. Structures of the gold-free ligands were geometry optimized using DFT calculations and studied in complex with the EGFR kinase domain (L858R/T790M mutant) (PDB-ID: 2JIV). In these experiments, a scaffold was identified that produces energetically favorable binding geometries in which the thiourea sulfur of the TKI is positioned in close proximity (4-4.5 Å) to the sulfur atom of cysteine-797. This orientation was considered compatible with electrophilic attack of the metal in a corresponding gold(I)-modified TKI on the protein thiol.

From the modeling studies, two structures, 4 and 5 (see Scheme 1), emerged, which were considered viable candidates for the desired application. The two derivatives (and all other derivatives reported) were synthesized from common intermediate 3, which was generated by installing a 3-chloro-4-fluoroanilino group at the 4-position of the quinazoline ring in precursor 1 and subsequent reduction of the 6-nitro group in 2 to a 6-amino group. Reaction of 3 with the appropriate isothiocyanates afforded the N,N'-disubstituted thiourea derivatives 4 and 5.

Scheme 1 Synthesis of quinazoline derivatives.

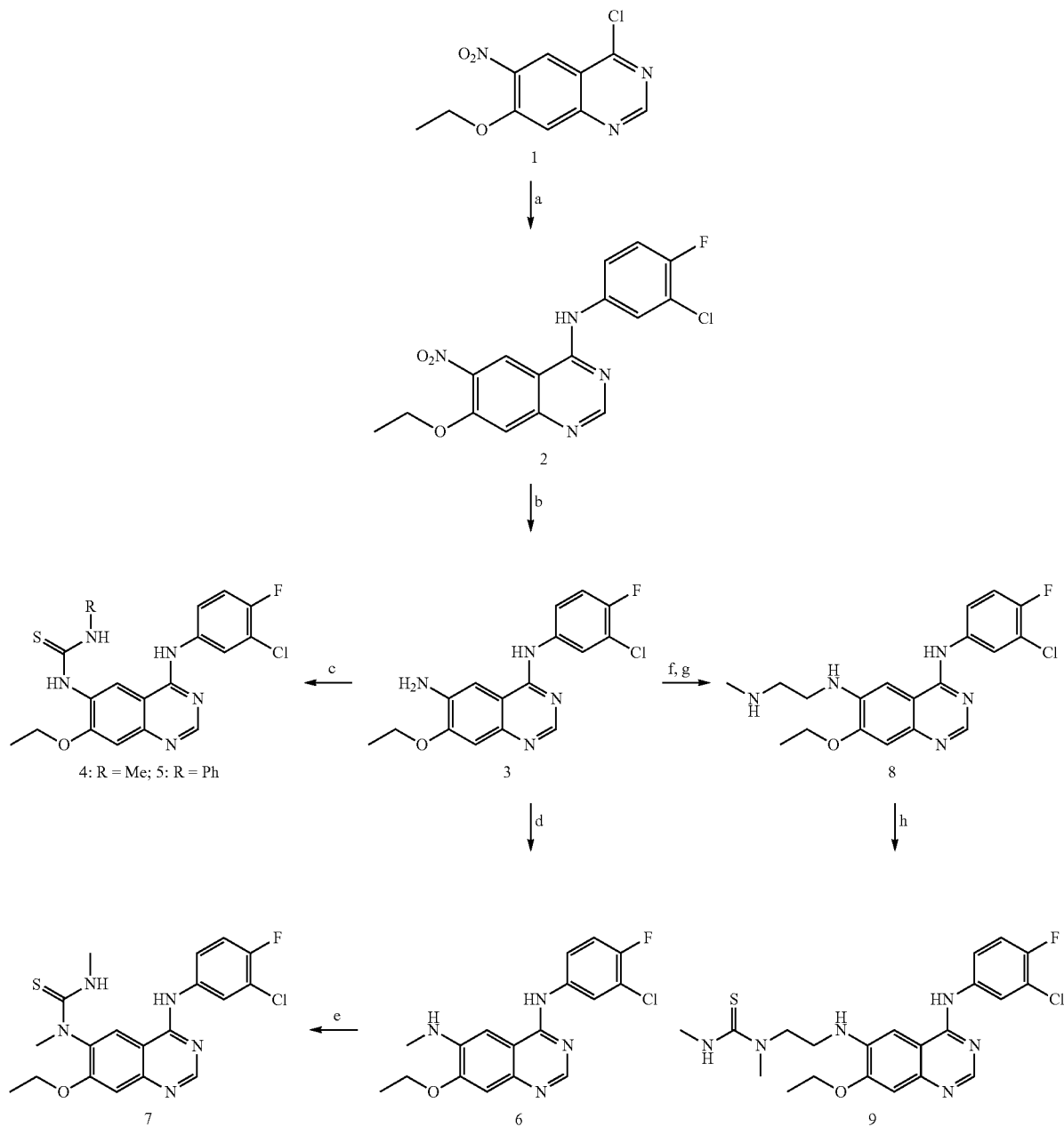

Reagents and conditions: a) 3-chloro-4-fluoroaniline, i-PrOH, rt, overnight; b) Fe, AcOH, NaOAc, MeOH, reflux, 3 h; c) RNCS, EtOH, rt, 3 h; d) paraformaldehyde, NaOMe, NaBH4, MeOH, reflux, 4 h; e) MeNCS, DMAP, EtOH, reflux, 30 h; f) tert-butylmethyl(2-oxoethyl)carbamate, NaCNBH3, AcOH, MeOH, rt, 2 h; g) 4M HCl, reflux, 2 h; h) MeNCS, EtOH, rt, 1 h.

Attempts to introduce gold(I) electrophiles such as [AuX] (where X=Cl— or SCN—) into these structures using the common precursor [AuX(tht)] (tht=tetrahydrothiophene), led to a product that was not isolatable (Scheme 2). Electrospray ionization mass spectra (ESI-MS) of these reaction mixtures showed little sign of the desired ligand exchange to produce complexes [AuX(4,5)], but were consistent with decomposition of 4 and 5 resulting in the analogous cyanamides (loss of $H_2S$, based on $[M-34+H]^+$ fragment ions) and gold(I) sulfide. Desulfuration of (aromatic) N,N'-disubstituted thioureas has previously been observed in the presence of heavy metals.

To circumvent the problem of ligand desulfuration, an N,N,N'-trisubstituted derivative 7 was synthesized from the N6-methylquinazoline derivative 6, which was generated from intermediate 3 via reductive amination. In reactions with [AuX(tht)], compound 7 showed greatly improved ligand properties and was able to act as a stable sulfur-donor. X-ray crystallographic and mass spectrometric analysis of the product isolated from the reaction mixtures indicated that compound 7 does not act as a terminal S-donor ligand in the desired complexes [AuX(7)]. Instead, 7 produces dinuclear complexes $[\{Au(7)\}_2]X_2$ in which 7 acts as a bridging ligand (see 12a and 12b in Scheme 2).

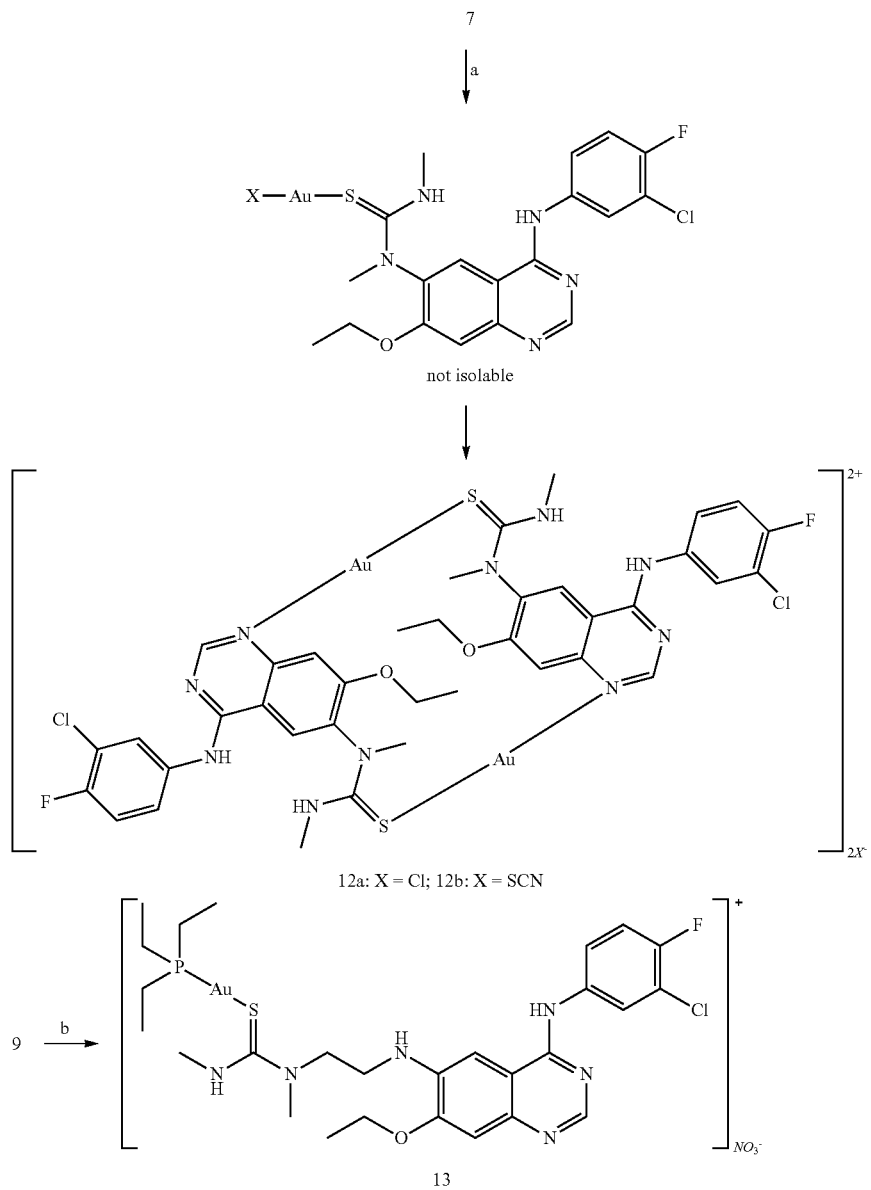

Scheme 2 Synthesis of gold(I) complexes.

12a: X = Cl; 12b: X = SCN

Reagents and conditions: a) [AuX(tht)] (10) tht = tetrahydrothiophene, CH$_2$Cl$_2$, rt, 30 min; b) [AuCl(PEt$_3$)] (11), MeOH/THF, AgNO$_3$, rt.

Figure 2:
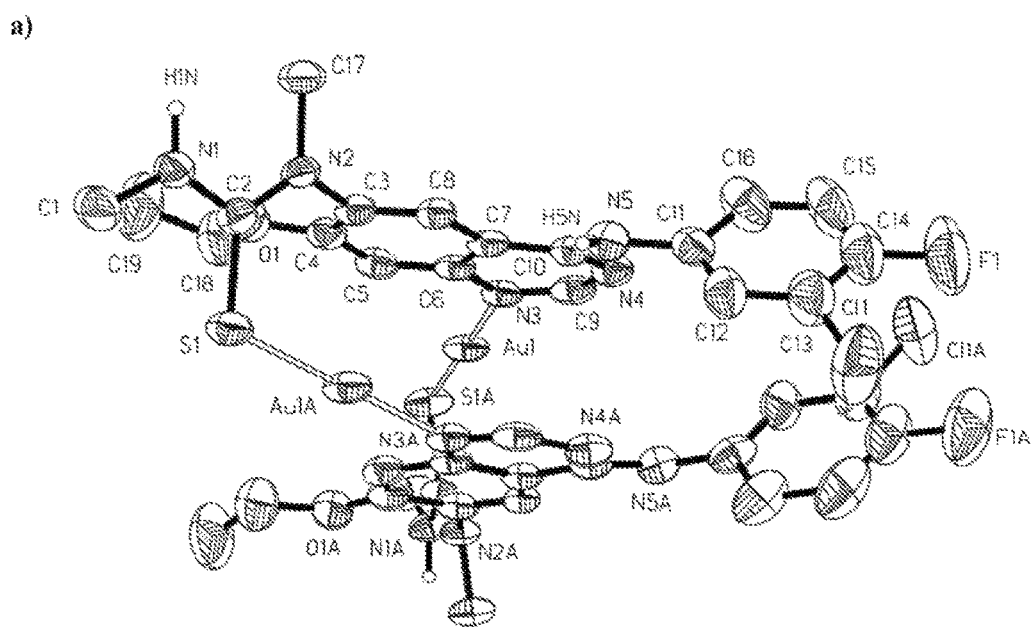
FIG. 2 (a) shows the structure of $[\{Au(7)\}_2]Cl_2 \cdot DMF$ (12a.DMF) in the solid state with selected atoms labeled. Counter ions and crystal solvent have been omitted for clarity. (b) shows electrospray ionization mass spectrum recorded in positive-ion mode of dinuclear complex 12a. Characteristic ions: m/z 420.3 $[M(7)+H]^+$, 518.3 $[M(12a)-Au+H]^{2+}$, 616.3 $[M(12a)-2Cl]^{2+}$, 1035.5 $[M(12a)-Au]^+$.
Figure 2:
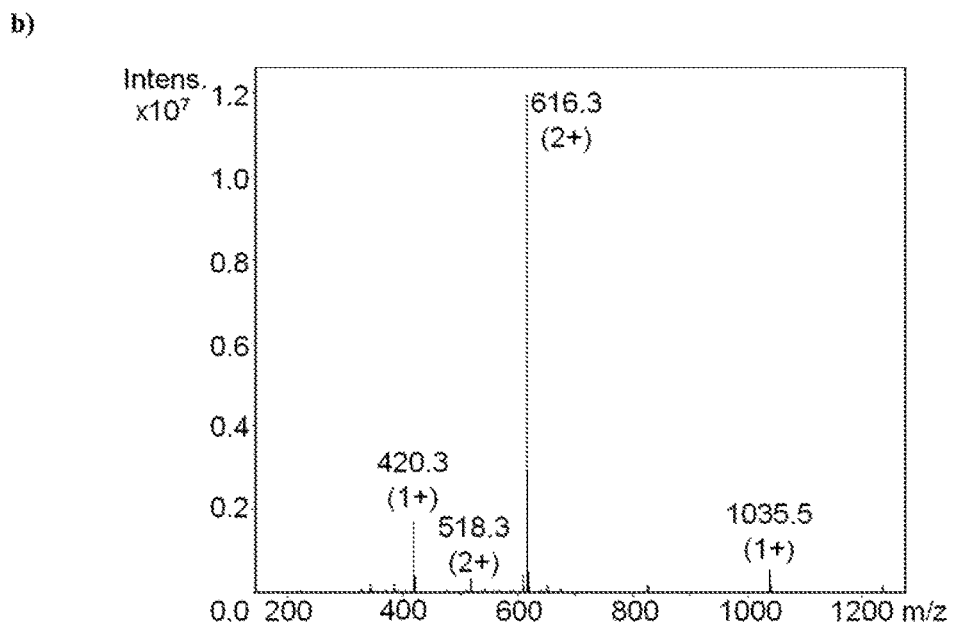

In the solid state structure of 12a, the Au(Q) centers are coordinated by a thiourea-S atom of one ligand and endocyclic quinazoline-N1 of another ligand. This produces an unusual arrangement in which the aromatic moieties of the two bridging ligands are mutually stacked at van der Waals distance (see FIG. 2a). Proton NMR chemical shift anomalies in conjunction with electrospray mass spectra recorded in positive-ion mode (see FIG. 2b) confirm that the dinuclear cationic structures persist in solution and are not solely a consequence of packing effects in the solid state. Importantly, no reversal of the dinuclear structure was observed when 12a was incubated under physiologically relevant concentrations in phosphate-buffered saline (containing ~14 mM chloride) for several days (data not shown). This observation suggests that 12a cannot be considered a cleavable precursor of the corresponding mononuclear complex, [AuCl(7)].

Attempts to install a more inert phosphine ligand in place of X via reaction of 7 with [AuCl(PEt$_3$)][15] to avoid substitution of the ligand trans to sulfur by quinazoline nitrogen were unsuccessful (no substitution of chloride by thiourea was observed). The latter reaction succeeded when the trisubstituted thiourea moiety was incorporated into an extended side chain at the 6-position of the quinazoline scaffold. Introduction of the (2-methylamino)ethyl group involved reductive amination of 3 to give 8, which was finally converted to thiourea 9 with isothiocyanate. While 9 did not yield the desired gold-modified mononuclear derivative when reacted with [AuX(tht)], it produced the cationic complex [Au(PEt$_3$)(9)](NO$_3$) (compound 13) (see Scheme 2), which proved to be stable with respect to desulfuration and dinucleation (based on ESI-MS and NMR data). Characteristic variations in $^1$H NMR chemical shifts observed for complex 13 relative to ligand 9 confirm selective binding of the {Au(PEt$_3$)}$^+$ moiety to thiourea sulfur.

Biological Activity

Cell proliferation assays in two NSCLC cell lines were performed to assess the cell growth inhibitory effects of the newly synthesized TKI derivatives 7 and 9 alone and as ligands in complexes 12a, 12b, and 13. For comparison the clinical drug gefitinib was included in the screening. The cell line NCI-H460 is a model of a large-cell carcinoma and is characterized by wild-type EGFR-TK. By contrast, NCI-H1975 adenocarcinoma cells harbor a point mutation (L858R) in exon 21 as well as a secondary mutation (T790M) at the bottom of the hydrophobic ATP binding pocket. While the former somatic (activating) mutation sensitizes cancer cells to EGFR-TKIs (including gefitinib), the latter causes resistance to these therapies.

The results of the cell proliferation assays are summarized in Table 1. Both NCI-H460 (wild-type) and NCI-H1975 (mutated) show the expected resistance to gefitinib with inhibitory concentrations in the high micromolar range, in agreement with previously reported data (typically, IC$_{50}$>10 µM[2b]). NCI-H460 cells were found to be more sensitive to all of the analogues tested than NCI-H1975, except for compound 9. The new analogue 7 was the least active compound tested with high-micromolar IC50 values in a range previously observed for structurally related thiourea-modified TKIs. By contrast, extension of the side chain on carbon-6 of the quinazoline ring to generate 9 led to a pronounced increase in potency, in particular in NCI-H1975, where a cytotoxic enhancement of 30-fold is observed. Most notably, compound 9 partially overcomes the acquired resistance against gefitinib observed in this cancer model. The low-micromolar inhibitory concentration determined for compound 9 in resistant NCI-H1975 compares favorably with the high-nanomolar/low-micromolar activity typically observed for gefitinib in sensitive NSCLC models. Modification of compounds 7 and 9 with {AuX} and {Au(PEt$_3$)}$^+$ groups, respectively, had only a minor effect on the inhibitory concentrations, with compound 13 maintaining low-micromolar activity in both cell lines.

TABLE 1

Summary of Cytotoxicity Data (IC$_{50}$ Values)[a]

| Compd | NCI-H460 | NCI-H1975 |
|---|---|---|
| 7 | 36.0 ± 4.4 | 51.7 ± 1.1 |
| 9 | 4.2 ± 0.4 | 1.7 ± 0.1 |
| 12a | 19.1 ± 2.0 | 39.7 ± 1.7 |
| 12b | 20.1 ± 0.2 | 31.9 ± 0.4 |
| 13 | 1.9 ± 0.1 | 2.5 ± 0.1 |
| gefitinib | 14.2 ± 0.5 | 30.0 ± 1.3 |

[a]IC$_{50}$ values ± S.D. (µM) were extracted from drug-response curves for two experiments performed in triplicate for each concentration.

Mechanistic Implications

Using simple ligand substitution chemistry, which has been previously developed to generate mixed thiourea-(pseudo)halido and thiourea-phosphine gold(I) complexes, a sulfur-modified TKI derived from gefitinib was introduced as a ligand. Compound 9 alone showed significantly better activity than gefitinib in a TKI-resistant cancer cell line. This observation suggests that the newly introduced thiourea-containing side chain may enhance the binding affinity of the classical TKI structure with the enzyme's active site. In the lowest-energy model generated for compound 9 in complex with EGFR-TK (L858R/T790M mutant) the thiourea-modified side chain is located in the hydrophilic region of the protein cleft produced by the bilobal kinase fold (see Supplementary Information). This orientation positions the thiourea-NH group in close hydrogen-bonding distance to residues Asn-842 and Asp-855, which may promote strong binding to the EGFR-TK domain.

The goal of turning compound 9 into a gold(I)-modified TKI was to further enhance the biological activity of the TKI by promoting reaction of cysteine-797 of the EGFR-TK with a targeted metal-based electrophile. Potential binding mechanisms of such a pharmacophore may involve cross-link formation between the protein and the ligand in the ATP binding pocket of the TKI, or complete transfer of the gold moiety from the TKI to the amino-acid sulfur (Scheme 3). Both types of irreversible modification have the potential to help overcome resistance mediated by reduced TKI binding affinity in the T790M mutant as a consequence of secondary mutations in the active site of the kinase. Unfortunately, unlike thiourea sulfur in compound 7, the corresponding side chain in 9, while conformationally more flexible, appears to adopt an unfavorable orientation for this application (S$_{thiourea}$----S$_{Cys-797}$≈9 Å). The ability of compound 9 to act as a targeted carrier of [Au(PEt$_3$)]$^+$ would also depend on the stability of the mixed thiourea-phosphine coordination in compound 13 in the presence of competing nucleophiles. These include sulfur-containing proteins in circulation and in the cytosol. Thiourea as a donor was chosen for its relative ease of synthesis and for its thiol-like properties and ability to compete with thiolate sulfur in gold(I) coordination. Alternative gold-affinic ligands remain to be tested as part of a broader effort to establish structure-activity relationships in gold-modified EGFR-TKIs.

Scheme 3. Potential reactions of gold(I) with cysteine sulfur in the ATP binding site of EGFR-TK via gold(I) transfer (left side pathway) of gold(I)-mediated cross-link formation (right side pathway). The same concept applies to derivatives containing platinum(II) and other metals.

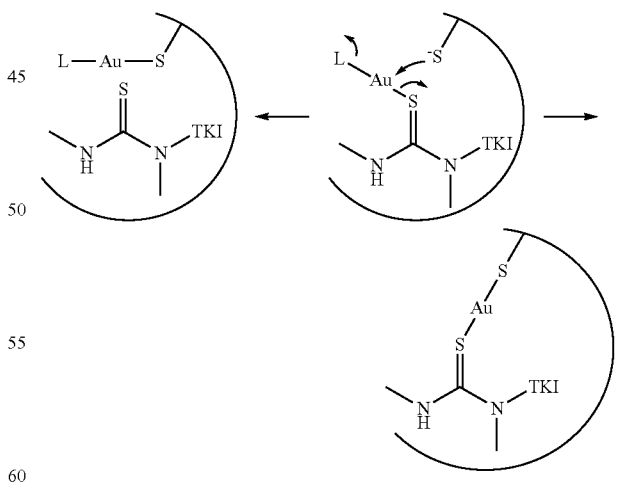

While the intention of the current design was to hijack gold into the ATP-binding pocket of the tyrosine kinase, a potential mechanism by which complex 13 disassembles into a gold-phosphine species and analogue 9 in the presence of reactive bioligands prior to reaching the enzyme active site has also to be considered. Gold(I)-phosphines directly target the mitochondria to trigger oxidative stress which leads to apoptosis. Aberrant EGFR expression is associated with defective mitochondrial apoptotic signaling, which renders affected cancer cells insensitive to conventional chemotherapy. Thus, a dual mechanism promoted by the individual components that involves inhibition of EGFR signaling and cell death triggered by mitochondrial toxicity may help overcome tumor resistance.

Derivative 9 showed promising activity in the cell proliferation assay, but attachment of the gold electrophile in 13 did not result in the desired enhancement in cell kill. One possible explanation for this observation would be that the $[Au(PEt_3)]^+$ group, while not compromising the binding affinity of the TKI moiety with the receptor, may be positioned unfavorably for reaction with the sulfur atom of cysteine-797. It is also possible that cytotoxic gold-phosphine species generated from complex 13 may not significantly contribute to the cell kill in the two cancer models, which may be dominated by TK inhibition.

Hydrogen tetrachloroaurate trihydrate was purchased from Alfa Aesar. The tetrahydrothionphenegold(I) complexes 10a and 10b,[13] chlorotriethylphosphinegold(I) 11, [15] compound 1,[12] and tert-butylmethyl(2-oxoethyl)carbamate[16] were synthesized using published procedures. For the preparation of biological buffers, biochemical grade chemicals (Fisher/Acros) were used. HPLC-grade solvents were used for all HPLC and mass spectrometry experiments. Reagents and chemicals were acquired from common vendors and used without further purification. Reactions involving gold were performed and solutions stored in the dark.

$^1$H NMR spectra of the target compounds and intermediates were recorded on Bruker Advance 300 and DRX-500 instruments. $^{13}$C NMR spectra were recorded on a Bruker DRX-500 instrument operating 125.8 MHz. Chemical shifts (8) are reported in parts per million (ppm) relative to tetramethylsilane (TMS). Electrospray ionization mass spectra (ESI-MS) were recorded on an Agilent 1100LC/MSD trap instrument. Ion evaporation was assisted by a flow of $N_2$ drying gas (300-350° C.) at a pressure of 40-50 psi and a flow rate of 11 L/min. Mass spectra were typically recorded with a capillary voltage of 2800 V over a mass-to-charge (m/z) scan range of 200-2200. The purity and stability of the target compounds was analyzed by reverse-phase high-performance liquid chromatography (HPLC) using the LC module of the Agilent Technologies 1100 LC/MSD trap system equipped with a multi-wavelength diode-array detector. Separations were accomplished with a 4.6 mm×150 mm reverse-phase Agilent ZORBAX SB-C18 (5 Mm) analytical column at 25° C. Separations were accomplished with the following solvent system: solvent A—optima water/0.1% formic acid; solvent B—methanol/0.1% formic acid; solvent C—acetonitrile/0.1% formic acid. Separations were performed at a flow rate of 0.5 mL/min and a gradient of 50% A/50% B to 5% A/95% B over 20 min (for 7), and at a flow rate of 0.5 mL/min and a gradient of 95% A/5% C to 5% A/95% C over 20 min (for 9). HPLC traces were recorded over a wavelength range of 363-463 nm. High-resolution mass spectrometry (HRMS) was performed on a Thermo Scientific LTQ Orbitrap XL equipped with an electrospray ionization source. Single crystals of 7 were grown from a saturated solution in methanol, while crystals of 12 were grown by slow diffusion of diethyl ether into a concentrated DMF solution. HPLC peaks were integrated with MestReNova 8.1. For all organic ligands studied in cancer cells, an analytical purity of ≥95% was confirmed by reversed-phase HPLC. The purity of compounds 12 and 13 was determined by CHN elemental analysis (Intertek Pharmaceutical Services, Whitehouse, N.J.). Single-crystal X-ray data acquired for compounds 7 and 12a and experimental details of the structure solution and refinement have been deposited with the Cambridge Crystallographic Data Centre (Cambridge, U.K.) under deposition codes CCDC976611 and CCDC976612, respectively.

Computational Studies

The inhibitor structures were built in GaussView 4.0 (Semichem Inc., Shawnee Mission, K S, 2009). Structures were optimized at the rb3lyp level of theory using the 6-311** basis set in Gaussian 03 (Gaussian, Inc., Pittsburgh Pa., 2003).[22] Prior to docking studies, structures were checked in AutoDockTools 1.5.4 (The Scripps Research Institute, La Jolla, Calif.) for possible bond torsion errors, and appropriate Gasteiger charges were calculated and assigned as necessary. The crystal structure of EGFR (L858R/T790M mutant) from the Brookhaven Protein Data Bank (PDB ID: 2JIV) was used as the 3-D receptor structure for docking studies, and the active site coordination ranges were defined using the grid box in AutoDockTools. The inhibitor structures were then docked into the active site using AutoDock Vina.[23] Conformational searches were performed with an exhaustiveness setting of '9'. Results were evaluated based on relative docking energies.

Tested Compounds

New thiourea and amine-derivatives, T1 and T2 (see below for structures), have been synthesized and fully characterized. New metal-TK1 derivatives G1-T1, P3-T2, and P9-T2 have been synthesized and fully characterized (see below for structures).

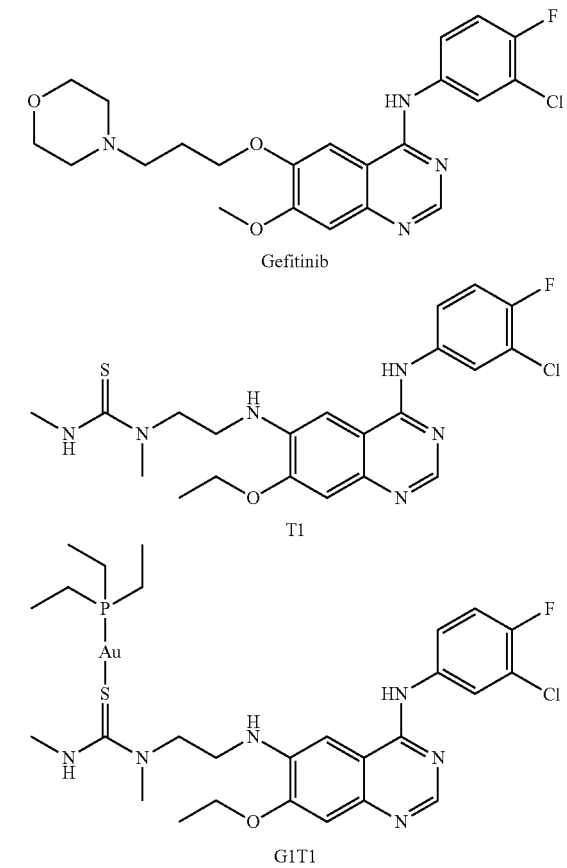

Gefitinib

T1

G1T1

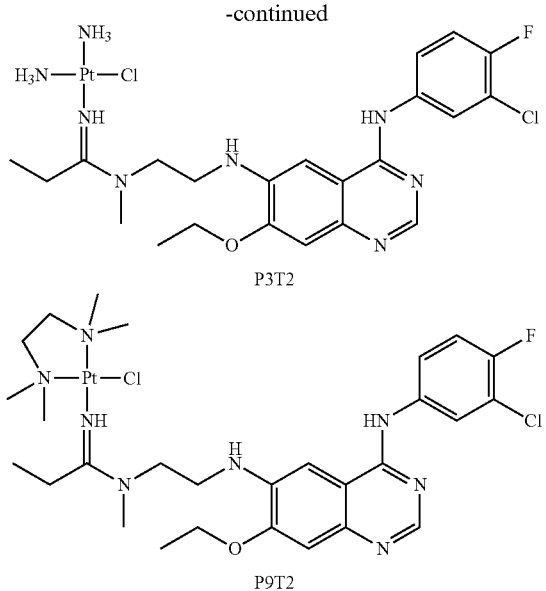

Compounds T1, G1-T1, P3-T2, and P9-T2 (see Scheme 4) have been tested in vivo in both NCI-H460 (wildtype EGFR) and NCI-H1975 (double-mutant EGFR) for biological activity. EGFR dissociation constants for P3-T2 and P9-T2 have been determined utilizing the KinomeScan at DiscoveRx Corporation (see Tables 2 and 3 below for $IC_{50}$ and $K_d$ values). Along with EGFR dissociation constants, a kinase selectivity assay was performed for P3-T2 by DiscoveRx utilizing 145 distinct kinases, which resulted in multiple selectivity "hits", mostly representing wildtype and mutant EGFR proteins.

TABLE 2

Summary of Cytotoxicity Data (IC50 Values)[a]

| Compound | NCI-H460[b] | NCI-H1975[c] |
|---|---|---|
| Gefitinib | 14.2 ± 0.5 | 30.0 ± 1.3 |
| T1 | 4.2 ± 0.4 | 1.749 ± 0.003 |
| G1T1 | 1.88 ± 0.09 | 2.45 ± 0.06 |
| P3-T2 | 12 ± 2 | 61 ± 5 |
| P9-T2 | >100 | >100 |

[a]$IC_{50}$ values ± S.D. (μM) were extracted from drug-response curves for two experiments performed in triplicate for each concentration.
[b]Wildtype EGFR (sensistive)
[c]L858R and T790M EGFR Mutations (resistant)

TABLE 3

Summary of $K_d$ Values Obtained[a]

| Compound | WT-EGFR[b] |
|---|---|
| Gefitinib[d] | 0.90 |
| P3T2[e] | 1 |
| P9T2[e] | 3.4 |

[a]Inhibitor dissociation constants (nM)
[b]Wildtype EGFR
[c]L858R and T790M EGFR Mutations
[d]Obtained from Fabian et. al. *Nature Biotechnology*, 23, 329-336 (2005). (DiscoverX)
[e]Obtained from DiscoveRx Lead Hunter (see Attachment # - DiscoveRx Final Reports)

Scheme 4

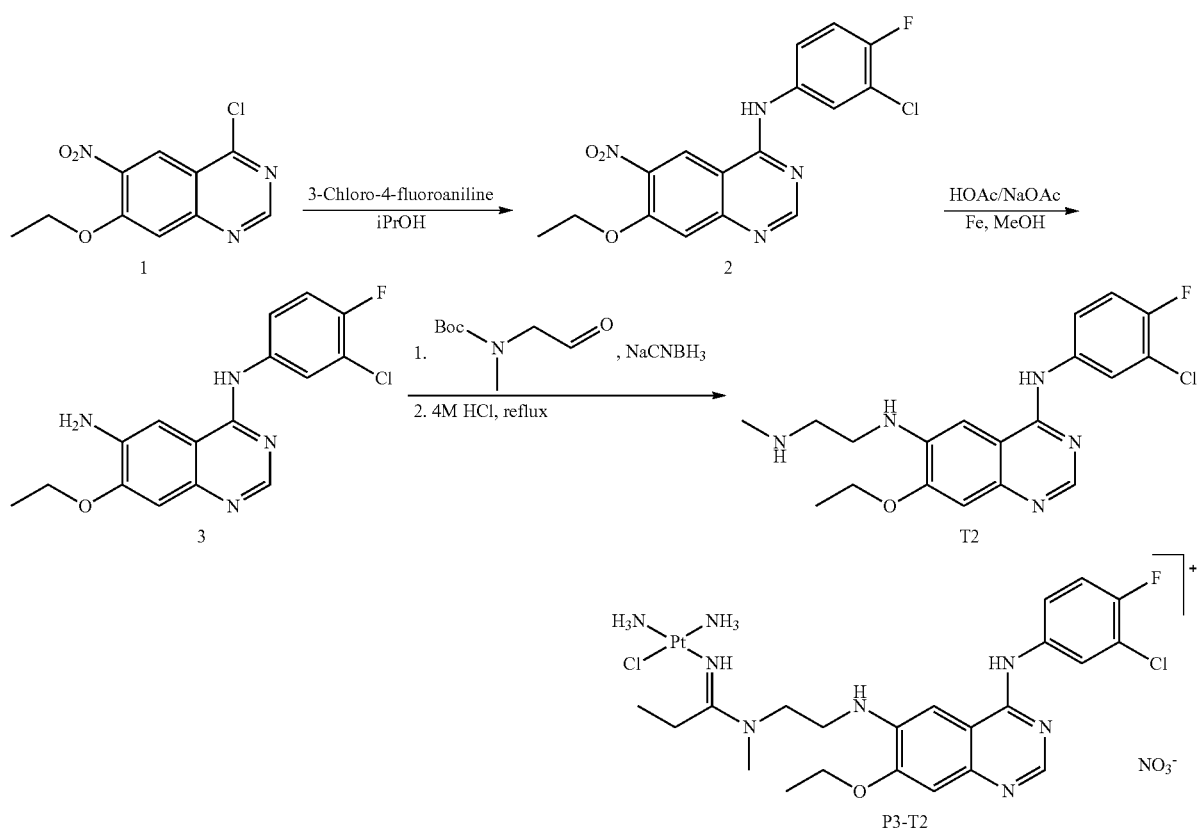

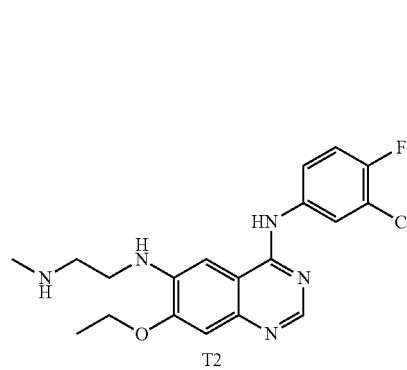
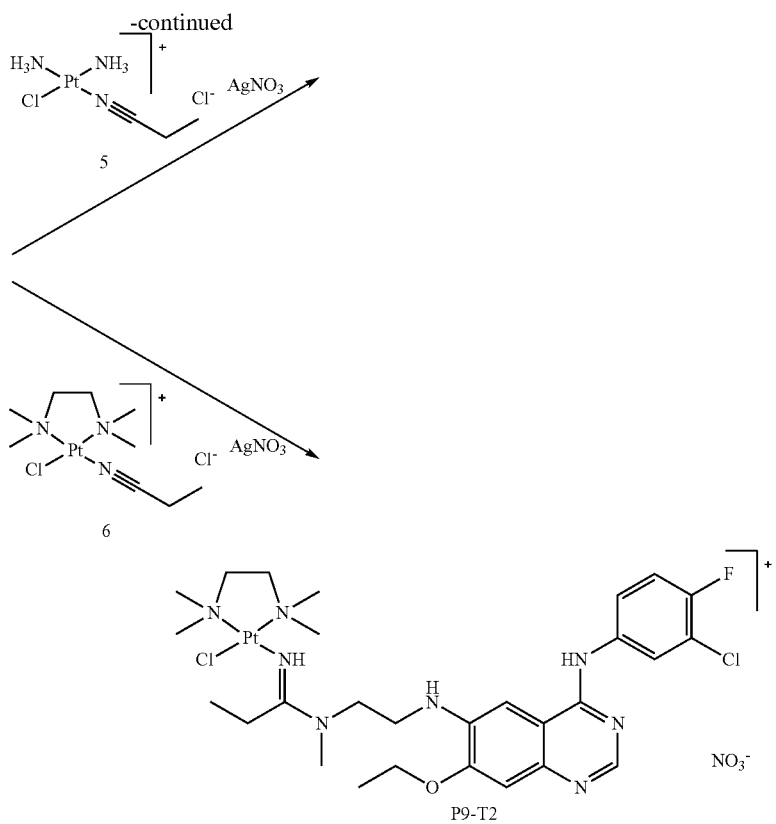
Compounds to be Tested
Compounds T3 (see Scheme 5) and T4 (see Scheme 6) and their platinum derivatives are being synthesized. Biological testing will be completed in NCI-H460 and NCI-H1975 cell lines. All Platinum-TKI derivatives will be tested in SKBR3 cells this spring to determine their utility in Her2-positive breast cancer as irreversible Her2 inhibitors.
Scheme 5
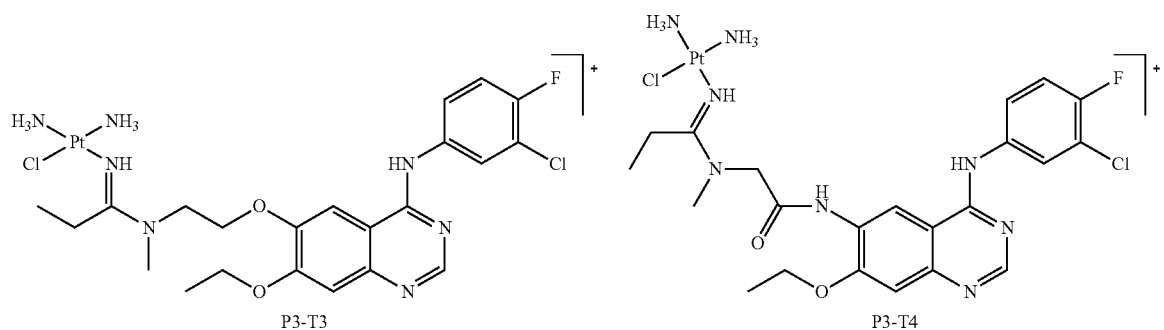
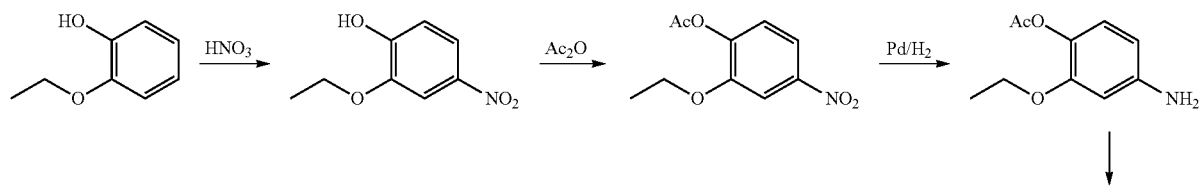

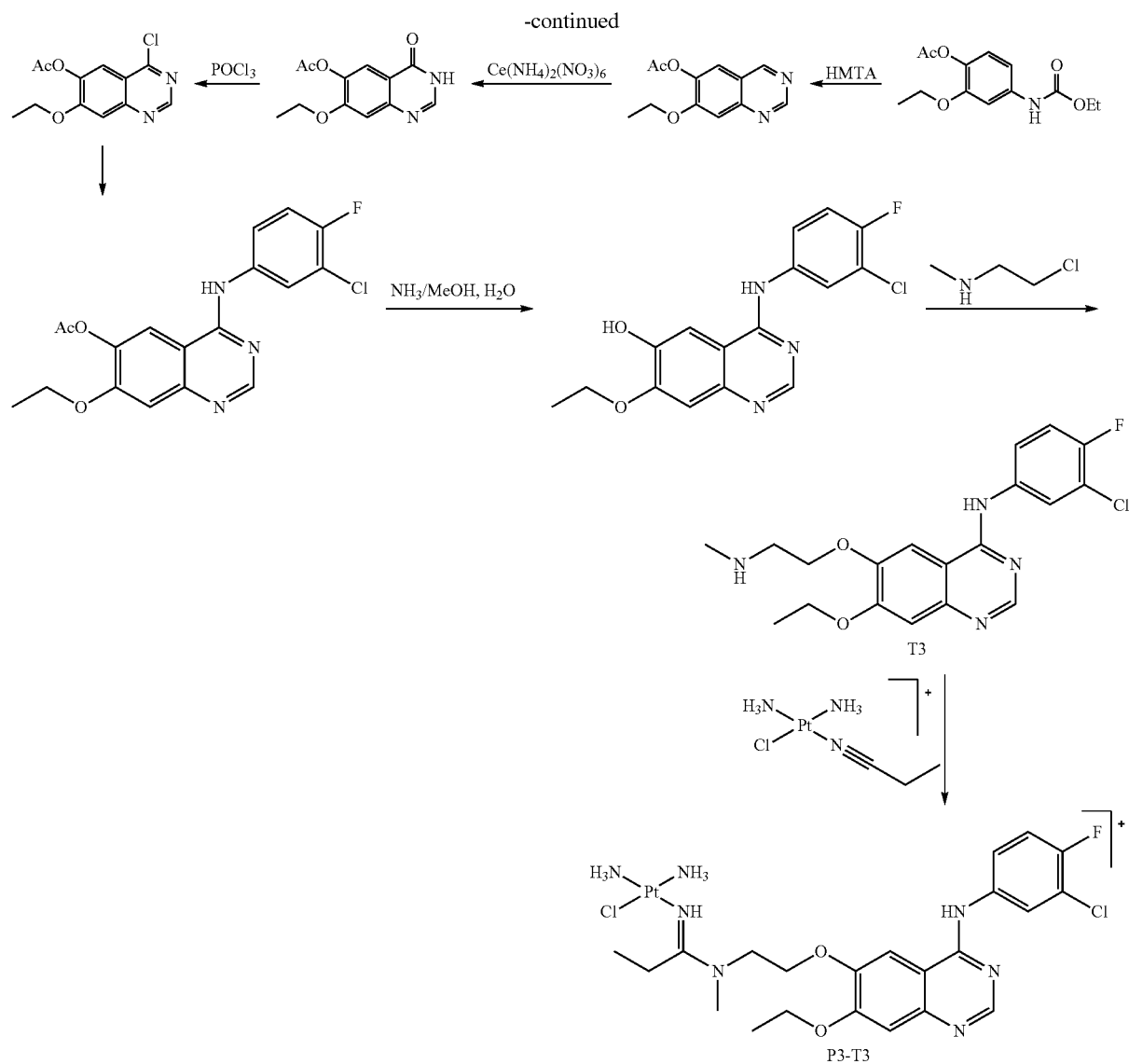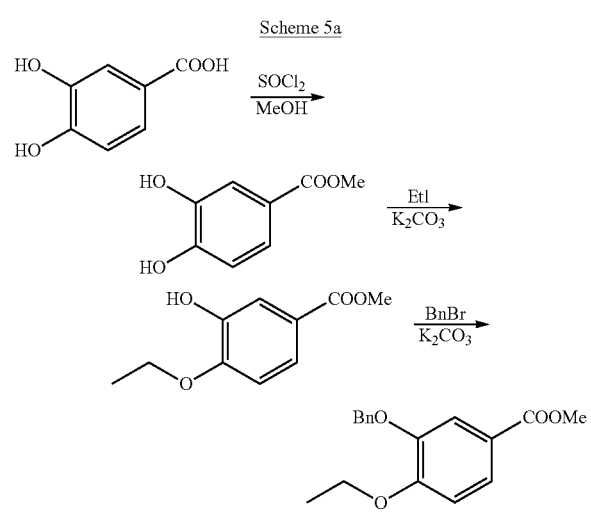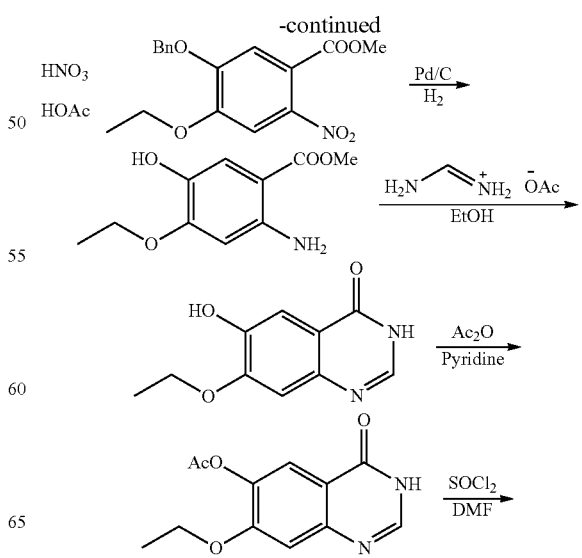

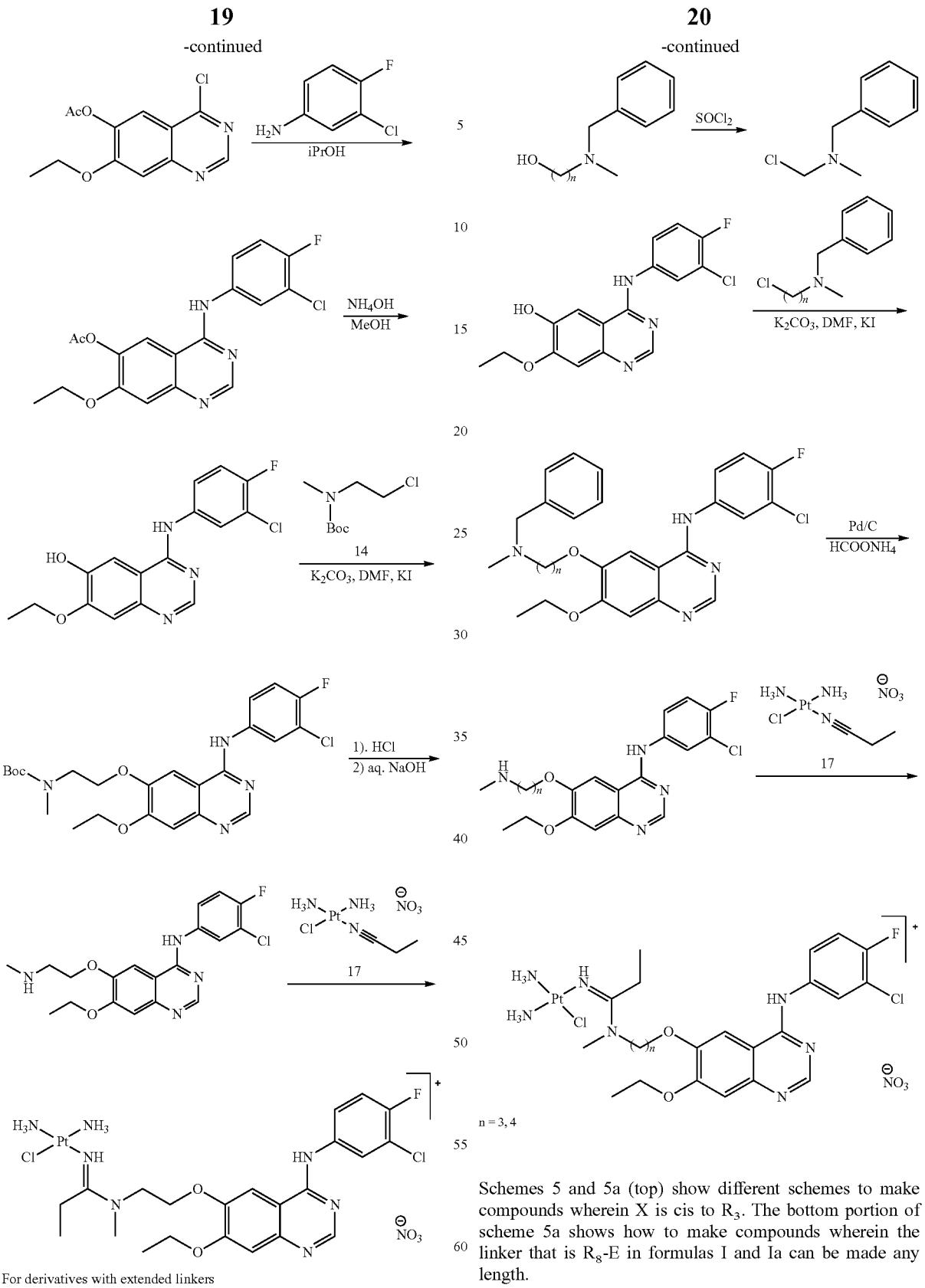
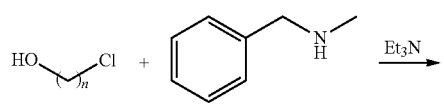

Schemes 5 and 5a (top) show different schemes to make compounds wherein X is cis to $R_3$. The bottom portion of scheme 5a shows how to make compounds wherein the linker that is $R_8$-E in formulas I and Ia can be made any length.

In an embodiment, scheme 5b shows how one can vary the structural diversity in chemical libraries by performing reactions at different temperatures. In an embodiment, the ratio of nitrile substitution vs. nitrile addition can be varied by varying the temperature.

Scheme 5b
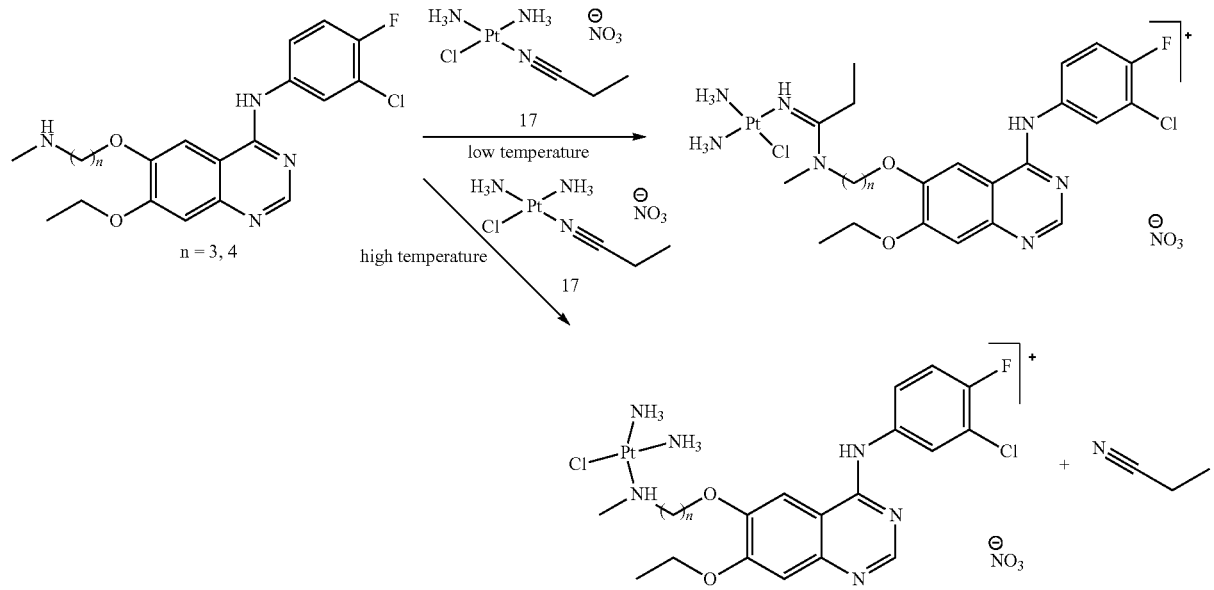
Scheme 6
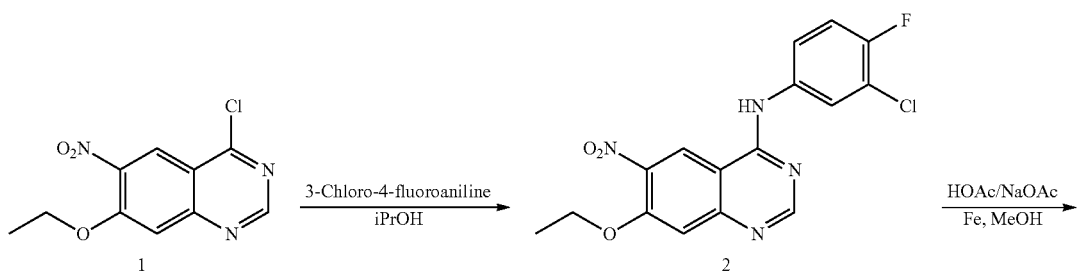
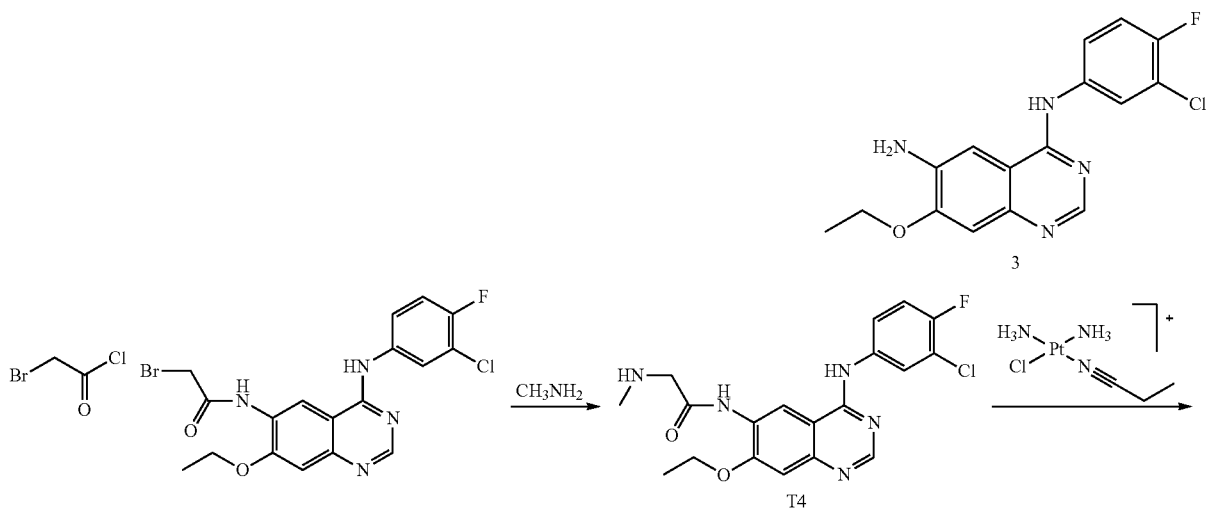

-continued

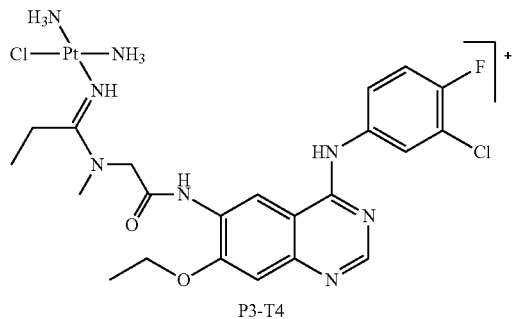

P3-T4

It should be noted that for the reactions in schemes 4-6, the outcome products of the reactions can be varied by varying the temperatures with either the nitrile substitution product or the nitrile addition product as the major component (for an example, see scheme 5b).

In one embodiment, the design using metal-based electrophiles has a fundamental advantage over Michael-acceptor-based inhibitors (such as afatinib): with the latter structures only active-site cysteine residues can be effectively targeted. In contrast, platinum forms stable bonds with many other amino-acid residues, such as methionine, histidine, and lysine, as well as nitrogen of the peptide backbone. In addition, in one embodiment, the present design can be tailored for use with other kinases. This includes enzymes involved in the escape mechanisms that confer resistance to EGFR (e.g. FGFR1) and kinases that cannot be targeted with current irreversible drugs because their active sites do not have targetable cysteines.

Preparation of Compounds

N-(3-Chloro-4-fluorophenyl)-7-ethoxy-6-nitroquinazolin-4-amine (2). A mixture of 1 (4.55 g, 18.0 mmol) in 40 mL of dichloromethane (DCM) and 3-chloro-4-fluoroaniline (2.61 g, 18.0 mmol) in 80 mL of isopropanol was stirred at room temperature overnight. The solid was collected and washed with small amount of DCM to give 6.67 g (93%) of 2 as a bright yellow powder. $^1$H NMR (300 MHz, DMSO-d6) δ 11.69 (bs, 1H), 9.59 (s, 1H), 8.93 (s, 1H), 8.07 (dd, J=6.8, 2.6 Hz, 1H), 7.77 (ddd, J=9.0, 4.4, 2.6 Hz, 1H), 7.63 (s, 1H), 7.54 (t, J=9.1 Hz, 1H), 7.27 (q, J=8.8 Hz, 1H), 4.39 (q, J=6.9 Hz, 2H), 1.44 (t, J=6.9 Hz, 3H); $^{13}$C NMR (126 MHz, DMSO-d6) δ 159.45, 156.29, 155.51, 154.99, 154.34, 139.92, 134.79, 126.18, 124.92, 123.34, 119.75, 117.54, 107.29, 105.92, 99.98, 66.76, 14.50; MS (ESI) m/z 363.1 [M+H]$^+$.

N$^4$-(3-Chloro-4-fluorophenyl)-7-ethoxyquinazoline-4,6-diamine (3). A mixture of 2 (2 g, 5 mmol), iron (1.68 g, 30.1 mmol), acetic acid (1.8 g, 30.1 mmol), and sodium acetate (0.41 g, 5.0 mmol) in 80 mL of methanol was refluxed for 3 h. To this mixture were added 3 mL of conc. ammonia. The mixture was filtered while hot, the solid washed with hot methanol, and the solvent removed from the filtrate by rotary evaporation. The resulting solid was extracted four times with hot acetone. After the acetone was removed from the extracts, water was added to the residue and the slurry was stirred for 30 min. The yellow precipitate was filtered, washed with water, and dried in a vacuum at 60° C. to yield 1.42 g (85%) of 3. $^1$H NMR (300 MHz, DMSO-d6) δ 9.38 (s, 1H), 8.38 (s, 1H), 8.25-8.11 (m, 1H), 7.90-7.73 (m, 1H), 7.38 (m, 2H), 7.08 (s, 1H), 5.33 (s, 2H), 4.22 (q, J=7.2 Hz, 2H), 1.45 (t, J=7.0 Hz, 3H); $^{13}$C NMR (126 MHz, DMSO-d6) δ 154.90, 153.51, 151.83, 151.58, 150.12, 144.70, 138.42, 137.46, 122.34, 121.34, 118.58, 116.38, 110.19, 106.24, 100.75, 63.77, 14.34; MS (ESI) m/z 333.1 [M+H]$^+$.

1-(4-((3-Chloro-4-fluorophenyl)amino)-7-ethoxyquinazolin-6-yl)-3-methylthiourea (4). A mixture of 0.1 g (0.3 mmol) of 3 and 0.033 g (0.45 mmol) of methylisothiocyanate was stirred in 3 mL of ethanol at room temperature for 3 h. The solution was concentrated to half its volume and stored in the refrigerator overnight. The precipitate formed was collected, washed with ethanol to yield 47 mg (39%) of 4. 1H NMR (500 MHz, DMSO-d6) δ 9.71 (s, 1H), 9.08 (s, 1H), 8.61 (s, 1H), 8.57 (s, 1H), 8.20 (dd, J=6.8, 2.6 Hz, 1H), 7.84 (ddd, J=9.2, 4.3, 2.7 Hz, 2H), 7.43 (t, J=9.1 Hz, 1H), 7.26 (s, 1H), 4.24 (q, J=7.0 Hz, 2H), 2.94 (d, J=4.3 Hz, 3H), 1.41 (t, J=6.9 Hz, 3H); $^{13}$C NMR (126 MHz, DMSO-d6) δ 182.39, 157.41, 157.17, 154.69, 154.52, 152.59, 150.42, 137.22, 128.17, 123.57, 122.48, 121.31, 119.26, 117.07, 109.16, 108.22, 64.79, 31.94, 14.83; MS (ESI) m/z 406.1 [M+H]$^+$.

1-(4-((3-Chloro-4-fluorophenyl)amino)-7-ethoxyquinazolin-6-yl)-3-phenylthiourea (5). This analogue was synthesized using the same procedure and stoichiometric amounts described for compound 4. Yield 35 mg (25%). $^1$H NMR (300 MHz. DMSO-d6) δ 9.95 (s, 1H), 9.74 (s, 1H), 9.36 (s, 1H), 8.72 (s, 1H), 8.57 (s, 1H), 8.19 (dd, J=6.9, 2.7 Hz, 1H), 7.83 (ddd, J=9.4, 4.4, 2.7 Hz, 1H), 7.56-7.30 (m, 5H), 7.27 (s, 1H), 7.16 (t, J=7.3 Hz, 1H), 4.26 (q, J=6.9 Hz, 2H), 1.43 (t. J=6.8 Hz, 3H); $^{13}$C NMR (126 MHz, DMSO-d6) δ 180.38, 156.97, 156.69, 154.19, 154.17, 153.99, 152.06, 149.99, 139.17, 136.66, 128.41, 128.06, 124.72, 124.06, 123.12, 122.01, 121.16, 118.70, 116.50, 108.48, 107.54, 64.31, 14.32; MS (ESI) m/z 468.2 [M+H]$^+$.

N$^4$-(3-Chloro-4-fluorophenyl)-7-ethoxy-N$^6$-methylquinazoline-4,6-diamine (6). To a solution of sodium methoxide in 30 mL of methanol (prepared from 0.35 g/15 mmol of sodium metal) were added 1 g (3 mmol) of 3 and 0.45 g (15 mmol) of paraformaldehyde. The reaction mixture was refluxed for 2 h and subsequently cooled to 0° C. After 0.57 g (15 mmol) of sodium tetrahydroborate were added in small portions, the orange mixture turned light yellow, and heating at reflux was continued for another 2 h. Solvent was removed by rotary evaporation and the residue was washed with water. The solid was then dissolved in a minimum amount of methanol/DCM (1:1), and the solution was passed through a Celite pad to remove a minor amount of a black solid. Solvent was removed to give 0.7 g (67%) of 6 as a light yellow powder. $^1$H NMR (300 MHz, DMSO-d6) δ 9.31 (s, 1H), 8.37 (s, 1H), 8.16 (dd, J=6.9, 2.7 Hz, 1H), 7.84 (ddd, J=9.1, 4.4, 2.6 Hz, 1H), 7.42 (t, J=9.1 Hz, 1H), 7.13 (s, 1H), 7.05 (s, 1H), 5.71 (q, J=5.1 Hz, 1H), 4.23 (q, J=6.9 Hz, 2H), 2.92 (d, J=4.9 Hz, 3H), 1.45 (t, J=6.9 Hz, 3H); $^{13}$C NMR (75 MHz, DMSO-d6) δ 154.77, 154.31, 151.69, 151.10, 149.94, 144.41, 139.89, 137.29, 122.83, 121.79, 118.67, 116.42, 110.15, 105.56, 95.67, 63.86, 30.03, 14.33; MS (ESI) m/z 347.1 [M+H]$^+$.

1-(4-((3-Chloro-4-fluorophenyl)amino)-7-ethoxyquinazolin-6-yl)-1,3-dimethylthiourea (7). A mixture of 2.5 g (7.2 mmol) of 6, 1.05 g (14.4 mmol) of methylisothiocyanate, and 1.76 g (14.4 mmol) of 4-dimethylaminopyridine (DMAP) in 20 mL of ethanol was stirred at reflux for 30 h. Additional methylisothiocyanate was added after 6, 18, and 24 h (2 eq each time). Ethanol was removed and the resulting dark oil was applied to a triethylamine-treated silica gel column. DCM/methanol (50:1) was used to remove nonpolar impurities and the same solvent at a 30:1 ratio was used to elute the product. The product fractions were combined, and solvent was removed by rotary evaporation. The residue was recrystallized from ethyl acetate to give 1.05 g (35%) of 7 as orange crystalline solid; $^1$H NMR (500 MHz, DMSO-d6) δ 9.72 (s, 1H), 8.61 (s, 1H), 8.48 (s, 1H), 8.23 (dd, J=6.9, 2.7 Hz, 1H), 7.85 (ddd, J=9.2, 4.3, 2.7 Hz, 1H), 7.44 (t, J=9.1 Hz, 1H), 7.33 (s, 1H), 7.18 (s, 1H), 4.24 (q, J=6.9 Hz, 2H), 3.47 (s, 3H), 2.85 (d, J=4.2 Hz, 3H), 1.36 (t, J=6.9 Hz, 3H); $^{13}$C NMR (126 MHz, DMSO-d6) δ 183.41, 158.43, 157.37, 155.44, 154.59, 152.66, 151.97, 137.07, 133.10, 124.53, 123.48, 122.35, 119.33, 117.13, 109.82, 109.68, 64.81, 56.49, 19.02, 14.81; HRMS m/z [M+H]$^+$ calcd for $C_{19}H_{20}ClFN_5OS$: 420.1061, found: 420.1032.

N4-(3-Chloro-4-fluorophenyl)-7-ethoxy-N6-(2-(methylamino)ethyl)quinazoline-4,6-diamine (8). A mixture containing 2.0 g (6.0 mmol) of 3, 0.68 g (18 mmol) of NaCNBH$_3$, and 2.1 g (12 mmol) of tert-butylmethyl(2-oxoethyl)carbamate in 40 mL of methanol was prepared. Sufficient glacial acetic acid (~1.5 g) was added until the solid was completely dissolved. A yellow precipitate formed after the reaction was stirred for 12 h at room temperature. Solvent was removed and the resulting oil was redissolved in DCM, washed with saturated NaHCO$_3$ and brine, and dried over Na$_2$SO$_4$. DCM was removed and the residue was heated at reflux in 50 mL of 4 M HCl for 2 h to remove the Boc protecting group. Acid was removed by rotary evaporation, and the resulting oil was allowed to solidify by stirring in ethanol at room temperature overnight. The solid was collected, washed with small amounts of ethanol, and partitioned between DCM and 1 M NaOH solution. The organic layer was recovered, washed with brine, and dried over Na$_2$SO$_4$. After the solvent was removed 1.0 g (51%) of 8 was obtained as a white solid. $^1$H NMR (300 MHz, DMSO-d6) δ 9.31 (s, 1H), 8.37 (s, 1H), 8.15 (dd, J=6.9, 2.6 Hz, 1H), 7.83 (ddd, J=9.1, 4.4, 2.7 Hz, 1H), 7.42 (t, J=9.1 Hz, 1H), 7.24 (s, 1H), 7.07 (s, 1H), 5.45 (t, J=5.4 Hz, 1H), 4.24 (q, J=6.9 Hz, 2H), 3.32 (q, J=5.8 Hz, 2H), 2.84 (t, J=6.0 Hz, 2H), 2.35 (s, 3H), 1.44 (t, J=6.9 Hz, 3H); $^{13}$C NMR (126 MHz, DMSO-d6) δ 154.82, 153.70, 151.77, 151.56, 150.16, 144.52, 138.77, 137.20, 122.93, 121.87, 118.63, 116.38, 110.04, 105.82, 96.42, 63.93, 49.75, 42.19, 35.81, 14.31; MS (ESI) m/z 390.2 [M+H]$^+$.

1-(2-((4-((3-Chloro-4-fluorophenyl)amino)-7-ethoxyquinazolin-6-yl)amino)ethyl)-1,3-dimethylthiourea (9). A mixture of 0.14 g (1.92 mmol) of methylisothiocyanate and 0.5 g (1.28 mmol) of 8 in 10 mL of ethanol was stirred at room temperature for 1 h to produce a white solid precipitate, which was collected, washed with cold ethanol, and dried to yield 0.53 g (90%) of 9. $^1$H NMR (500 MHz, DMSO-d6) δ 9.24 (s, 1H), 8.39 (s, 1H), 8.18 (dd, J=6.9, 2.7 Hz, 1H), 7.85 (ddd, J=9.1, 4.0, 2.7 Hz, 1H), 7.51 (q, J=4.2 Hz, 1H), 7.43 (t, J=9.1 Hz, 1H), 7.25 (s, 1H), 7.06 (s, 1H), 5.85 (t, J=5.3 Hz, 1H), 4.22 (q, 2H), 4.16 (t, J=6.4 Hz, 2H), 3.47 (q, J=6.0 Hz, 2H), 3.10 (s, 3H), 2.94 (d, J=4.1 Hz, 3H), 1.45 (t, J=6.9 Hz, 3H); $^{13}$C NMR (126 MHz, DMSO-d6) δ 182.50, 155.32, 154.22, 152.29, 152.17, 150.70, 145.11, 139.13, 137.76, 123.26, 122.19, 119.22, 116.99, 110.57, 106.31, 96.57, 64.51, 51.89, 41.95, 37.90, 33.19, 14.97; HRMS m/z [M+H]$^+$ calcd for $C_{21}H_{25}ClFN_6OS$: 463.1483, found: 463.1464.

[{Au(7)}$_2$]Cl$_2$ (12a). A mixture of 0.10 g (0.24 mmol) of compound 7 and 76 mg (0.24 mmol) of chlorotetrahydrothiophenegold(I) (10a) in 5 mL of DCM and 1 mL of methanol and was stirred at room temperature for 30 min. When the solution was concentrated to a volume of ~1 mL, compound 12a precipitated as an off-white solid, which was collected, washed with DCM, and dried in a vacuum at 60° C. Yield: 0.116 g (75%). $^1$H NMR (500 MHz, DMSO-d6) δ 9.77 (s, 1H), 8.89 (s, 1H), 8.63 (s, 1H), 8.54 (s, 1H), 8.23-8.15 (m, 1H), 7.86-7.78 (m, 1H), 7.46 (t, J=9.1 Hz, 1H), 7.33 (s, 1H), 4.25 (s, 2H), 3.53 (s, 3H), 3.17 (s, 3H), 1.45-1.30 (m, 3H); $^{13}$C NMR (126 MHz, DMSO-d6) δ 175.87, 157.60, 157.44, 155.79, 154.75, 152.81, 152.02, 136.88, 133.21, 124.09, 123.79, 122.59, 119.37, 117.19, 109.68, 65.09, 55.37, 34.21, 14.88: HRMS m/z [M]2+ calcd for $C_{38}H_{38}Au_2Cl_{12}F_2N_{10}O_2S_2$: 616.0648, found: 616.0611; anal. calcd for $C_{38}H_{38}Au_2ClF_2N_{10}O_2S_2 \cdot CH_2Cl_2$: C, 33.20, H, 2.71, N, 10.19, found: C, 33.49, H, 2.65, N, 10.13. (The analogous thiocyanate salt 12b showed the same mass spectroscopic and NMR features; no other details are reported.)

[Au(9)PEt$_3$](NO$_3$) (13). To 0.153 g (0.34 mmol) of 9 in a mixture of 10 mL of THF and 5 mL of methanol 0.122 g (0.34 mmol) of chlorotriethylphosphinegold(I) was added. The mixture was stirred for 5 min, and 56 µL of a 1 g/mL aqueous solution of AgNO$_3$ were added to exchange chloride with nitrate counter ions. Precipitated AgCl was filtered off and the filtrate was concentrated and added to 20 mL of diethyl ether. Compound 13 precipitates as a yellow solid, which was washed with diethyl ether and dried in a vacuum. Yield: 0.126 g (46%). $^1$H NMR (500 MHz, DMSO-d6) δ 9.32 (s, 1H), 8.41 (s, 1H), 8.27 (q, J=4.2 Hz, 1H), 8.15 (dd, J=6.8, 2.6 Hz, 1H), 7.83 (ddd, J=9.1, 4.0, 2.7 Hz, 1H), 7.44 (td, J=9.1, 0.8 Hz, 1H), 7.29 (s, 1H), 7.10 (s, 1H), 5.77 (t, J=5.35 Hz, 1H), 4.24 (q, J=6.9 Hz, 2H), 4.19 (t, J=5.6 Hz, 2H), 3.57 (q, J=6.1 Hz, 2H), 3.21 (s, 3H), 3.10 (d, J=4.0 Hz, 3H), 1.89 (dq, J=10.6, 7.6 Hz, 6H), 1.45 (t, J=6.9 Hz, 3H), 1.05 (dt, J=19.3, 7.7 Hz, 9H); $^{13}$C NMR (126 MHz, DMSO-d6) δ 175.45, 154.87, 153.77, 151.84, 151.76, 150.27, 144.14, 138.31, 137.01, 122.84, 121.78, 118.70, 116.49, 109.91, 105.65, 96.57, 64.05, 52.18, 40.8, 33.57, 16.78, 14.37, 8.94, 8.83; HRMS m/z [M]$^+$ calcd for $C_{27}H_{39}AuClFN_6OPS$: 777.1982, found: 777.1957, anal. calcd for $C_{27}H_{39}AuClFN_7O_4PS$: C, 38.65, H, 4.68, N, 11.67, found: C, 38.13, H, 4.25, N, 10.79.

Cell Proliferation Assay

The human non-small cell lung cancer cell lines, NCI-H460 (large cell) and NCI-H1975 (adenocarcinoma), were obtained from the American Type Culture Collection (Rockville, Md., USA). Both cell lines were cultured in RPMI-1640 media (HyClone) supplemented with 10% fetal bovine serum (FBS), 10% penstrep (P&S), 10% L-glutamine, and 1.5 g/L NaHCO$_3$. Cells were incubated at a constant temperature at 37° C. in a humidified atmosphere containing 5% CO$_2$ and were subcultured every 2 to 3 days in order to maintain cells in logarithmic growth. The cytotoxicity studies were carried out according to a standard protocol using the Celltiter 96 aqueous nonradioactive cell proliferation assay kit (Promega, Madison, Wis.). Stock solutions (10 mM) of all drugs were made in DMF and serially diluted with media prior to incubation with cancer cells. IC$_{50}$ values were calculated from dose-response curves using sigmoidal curve fits in GraphPad Prism (GraphPad Software, La Jolla, Calif.).

Thus, in an embodiment, the present invention relates to compounds, compositions and methods comprising the compounds of Formula I or Formula Ia:

FORMULA I

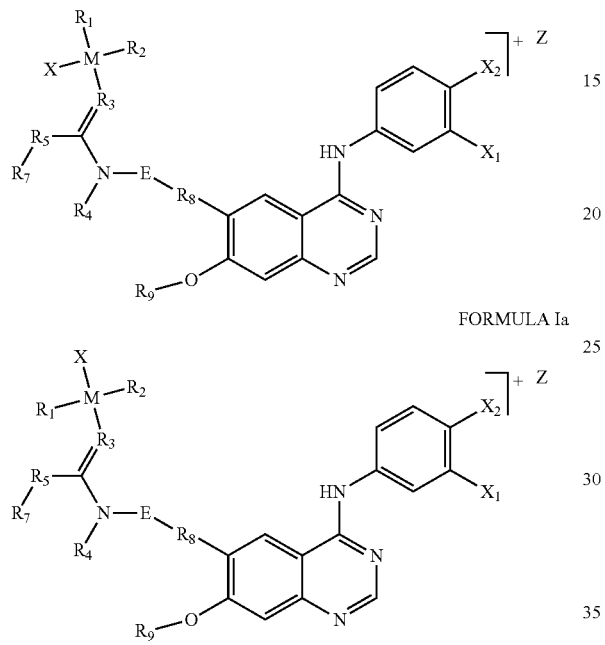

FORMULA Ia wherein X is halo, OH$^-$, H$_2$O, —OC(O)R$_9$, —P((—CH$_2$)qCH$_3$)$_3$, nitrate, sulfate or a carbene of structure

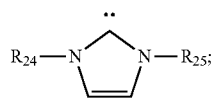

wherein q is 0, 1, 2, 3, 4, 5, or 6;

X$_1$ and X$_2$ are independently halo, C$_{1-6}$alkoxy, C$_{1-6}$alkyl, C$_{2-6}$alkynyl, nitro, amino, —NHC(O)(R$_{10}$), —NHC(O)O(R$_{10}$), —C(O)NHR$_{10}$, or —OC(O)NHR$_{10}$;

M is linear gold(I), square planar platinum(II), gold(III), or an octahedral metal including but not limited to platinum (IV), ruthenium(II), ruthenium(II), rhodium(III), iridium (III);

R$_1$ and R$_2$ are amino, ammonia or pyridine groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

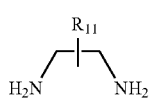

a

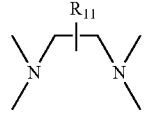

b

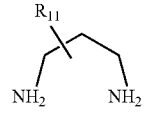

c

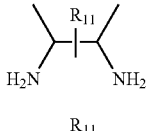

d

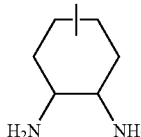

e

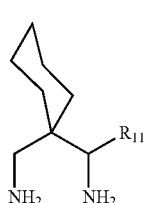

f

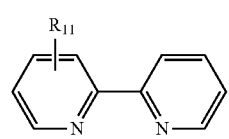

g

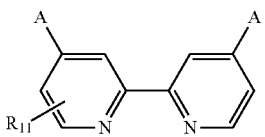

h wherein A is H, —CH$_3$, —OCH$_3$, CF$_3$ or NO$_2$;

R$_3$ is —N(R$_{26}$)— or S; wherein R$_{26}$ is hydrogen or C$_1$-C$_6$alkyl;

R$_4$ is hydrogen, C$_{1-6}$ alkyl, or CH$_2$—R$_{12}$;

E is —(CH$_2$)$_q$—;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_8$ is —NR$_{13}$—, —C(O) NR$_{13}$—, —NR$_{13}$C(O)—, —O—, —S—, —OC(O)—, and —C(O)O—

R$_{13}$ is —H or —C$_{1-6}$alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

$R_{11}$ and $R_{12}$ are independently hydrogen, hydroxyl, $C_{1-6}$ alkyl, —$OCH_3$, —$CF_3$, $NO_2$;

$R_{24}$ and $R_{25}$ are independently hydrogen or $C_{1-4}$alkyl; and

Z is independently one or more halo or nitro, or one or more counterions sufficient to balance the charge of the compound.

When M is an octahedral metal, it should be recognized that all possible geometric cis and trans isomers of X, R1, and R2 are possible. It should be noted that in one embodiment, other octahedral metals besides those listed above can potentially be used as a possible variables for M.

In an embodiment, when M is Au(I), the compounds, compositions and methods of the present invention that incorporate the formulas (compounds and compositions) of the present invention can be derived from compounds where X is trans to $R_3$.

In an embodiment, $X_1$ is F or Cl and $X_2$ is F or Cl. In an embodiment $X_2$ is F and $X_1$ is F or Cl. In an embodiment, $X_2$ is F or Cl and $X_1$ is Cl. In a variation, $X_2$ is F and $X_1$ is Cl.

In an embodiment, X is —P(—$CH_2$—$CH_3$)$_3$. In an embodiment, $R_3$ is —NH or S. In an embodiment, $R_5$ and $R_7$ together are ethyl or —$NHCH_3$. In an embodiment, $R_4$ is H or $CH_3$. In an embodiment, $R_{13}$ is H or $CH_3$. In an embodiment, E is methylene. In an embodiment, $R_9$ is methyl or ethyl. In a variation, $R_9$ is ethyl.

It should be understood that the methods, compounds and compositions of the present invention are generic. For example, the unique modular approach can be used to generate other ITKI pharmacophores targeting various cancer-related kinases. For example, the structure of WZ4002, an irreversible EGFR inhibitor and AVL-292, a Bruton's tyrosine kinase (BTK) inhibitor, a clinically approved drug, can be easily modified to allow attachment of a monofunctional platinum and/or gold moiety (see scheme 7—shown with platinum).

It should be understood that modifications can be made to the present invention without departing from the spirit and scope of the present invention. For example and in one embodiment, rather than having a quinazoline group as a central heterocycle, it is contemplated and therefore within the scope of the invention that a pyrimidine moiety, or a benzene moiety might occupy the position occupied by the quinazoline. For example, modifications might be made to known cancer drugs to add the platinum moiety using the methodology as disclosed in the present invention to produce modified derivatives of ponatinib, XZ4002 or to AVL-292 (or other known cancer drugs) as shown in scheme 7.

Scheme 7

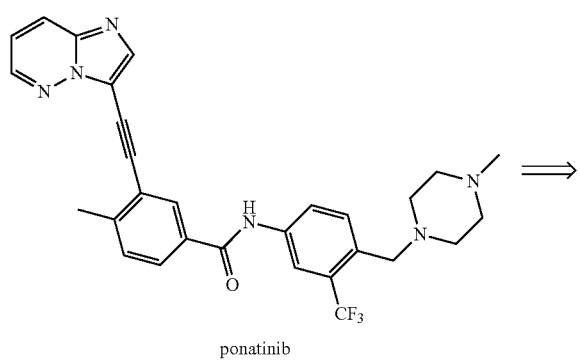

ponatinib

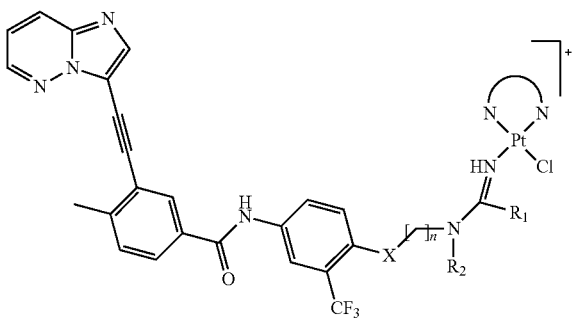

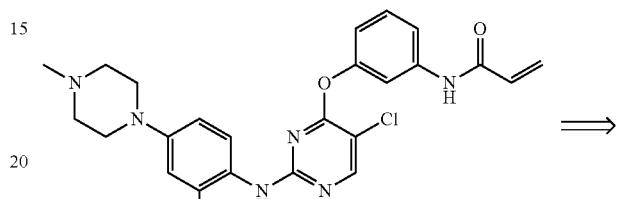

WZ4002

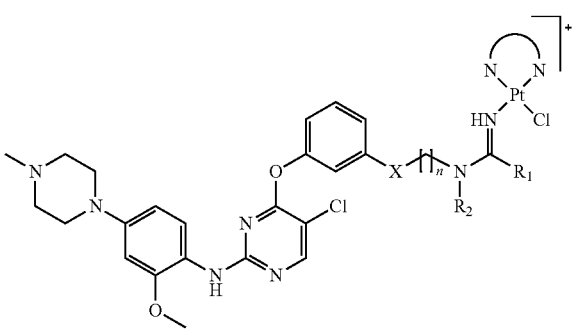

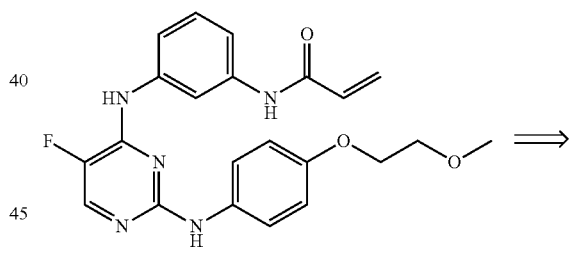

AVL-292

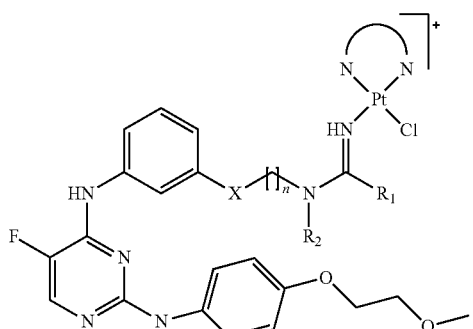

R1 = alkyl, ester
R2 = alkyl, aryl
N^N = en, pn, tmeda, (NH3)2, tmpda, (RR,RS,SS)-2,3-dabn
n = 0, 1, 2, 3
X = NH, NHC(O), CH2, O Accordingly, in an alternate embodiment, the compounds, compositions and methods of the present invention include compounds of Formula II:

FORMULA II

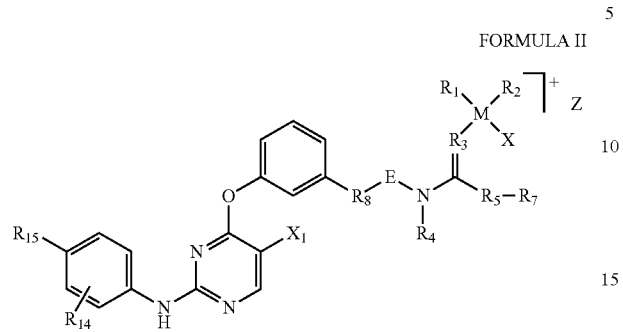

wherein X is halo, H$_2$O, —OC(O)R$_9$, —P((—CH$_2$)qCH$_3$)$_3$, nitrate or sulfate;
wherein q is 0, 1, 2, 3, 4, 5, or 6;
X$_1$ is independently halo, C$_{1-6}$alkoxy, C$_{1-6}$alkyl, C$_{2-4}$alkynyl, nitro, amino, —NHC(O)(R$_{10}$), —NHC(O)O(R$_{10}$), —C(O)NHR$_{10}$, or —OC(O)NHR$_{10}$;
M is Au or Pt and if M is Au, R$_1$ and R$_2$ are not present;
R$_1$ and R$_2$ are amino, ammonia or pyridine groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

a
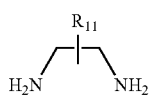

b
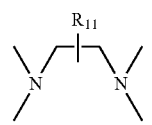

c
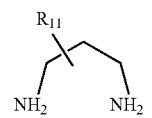

d
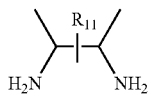

e
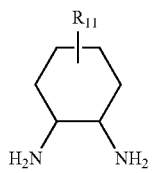

f
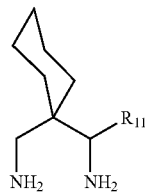

g
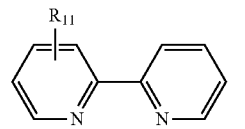

h
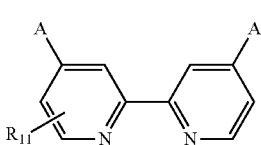

wherein A is H, —CH$_3$, —OCH$_3$, CF$_3$ or NO$_2$;
R$_3$ is —N(R$_{26}$)— or S; wherein R$_{26}$ is hydrogen or C$_1$-C$_6$alkyl;
R$_4$ is hydrogen, C$_{1-6}$ alkyl, or CH$_2$—R$_{12}$;
E is —(CH$_z$)$_q$—;
R$_5$ is a direct bond, —NH— or C$_1$-C$_6$alkylene;
or R$_5$ and X together with the atoms to which they are attached form a 6- or 7-membered ring, wherein said 6- or 7-membered ring contains a linking group —C(O)O— or —OC(O)—;
R$_7$ is hydrogen, methyl, —CH(R$_{17}$)(R$_{18}$), —C(O)O—R$_{18}$, or —OC(O)—R$_{18}$; wherein
R$_{17}$ is hydrogen or C$_{1-6}$ alkyl;
R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;
R$_{19}$ is hydrogen or C$_{1-6}$ alkyl;
R$_{20}$ is hydrogen, C$_{1-6}$ alkyl;
R$_8$ is —NR$_{13}$—, —C(O) NR$_{13}$—, —NR$_{13}$C(O)—, —O—, —S—, —OC(O)—, and —C(O) O—R$_{13}$ is —H or —C$_{1-6}$alkyl;
R$_{11}$ and R$_{12}$ are independently hydrogen, hydroxyl, C$_{1-6}$ alkyl, —OCH$_3$, —CF$_3$, NO$_2$;
R$_{14}$ is C$_{1-3}$alkoxy;
R$_{15}$ is N-methyl-piperazine or —O—(CH$_2$)$_{2-4}$OCH$_3$;
R$_{24}$ and R$_{25}$ are independently hydrogen or C$_{1-4}$alkyl;
and
Z is independently one or more halo or nitro, or one or more counterions sufficient to balance the charge of the compound.

In an embodiment, the present invention relates to compounds of Formulas I and/or II, to compositions (e.g., pharmaceutical compositions) containing those compounds and to methods of using those compounds.

Those of skill in the art will recognize that in formulas I and II, if M=Au and X=negatively charged residue, e.g., halide, there will be no counter ion, Z, and no net charge on the molecule.

In an embodiment, the pharmaceutical composition may contain pharmaceutically acceptable salts, solvates, and prodrugs thereof, and may contain diluents, excipients, carriers, or other substances necessary to increase the bioavailability or extend the lifetime of the compounds of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

The pharmaceutical compositions containing a compound of the invention may be in a form suitable for injection either by itself or alternatively, using liposomes, micelles, and/or nanospheres.

The pharmaceutical composition suitable for injection can be made as disclosed in Lammers, T. et al., J. Controlled Release, 161, 175-187 (2012), or in Barenholz, Y., J. Controlled Release, 160, 117-134, (2012), both of which are incorporated by reference in their entireties. Alternatively, compositions intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate.

The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising a compound of Formulas I and/or II or a salt thereof.

A solution of the invention may be provided in a sealed container, especially one made of glass, either in a unit dosage form or in a multiple dosage form.

Any pharmaceutically acceptable salt of a compound of Formulas I and/or II may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the compound of Formulas I and/or II is a hydrochloric acid salt including a mono, di, or trihydrochloride.

Any solvent which is pharmaceutically acceptable and which is able to dissolve the compounds of Formulas I and/or II or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water, sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes. e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose: mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise a compound of Formulas I and/or II or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the compound of Formulas I and/or II or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used is the ideal concentration to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising a compound of Formulas I and/or II or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving a compound of Formulas I and/or II or a pharmaceutically acceptable salt thereof in a pharmaceutically acceptable solvent. Where a pharmaceutically acceptable acid salt of a compound of Formulas I and/or II is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

In a further variation, the present invention contemplates combination therapies in which the compounds of the present invention can be used in conjunction with other cisplatin compounds. The efficacy of this combination therapy is likely to be enhanced because of the different mechanisms and modes of action that first generation cisplatin compounds exhibit relative to the compounds of the present invention. It is also contemplated and therefore within the scope of the invention that other anti-neoplastic agents/compounds can be used in conjunction with the compounds of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agents (e.g., specifically binding antibodies or antigen binding regions, or soluble TWEAK receptor antagonists. ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA); emaxanib, (Pfizer, USA); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA);

KM-2550, (Kyowa Hakko, Japan); SU-0879, (Pfizer, USA); CGP-79787, (Novartis, Switzerland); the ARGENT technology of Ariad. USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borcan, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation. USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University. USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors. (Xenova, UK); CEP 5214, (Cephalon. USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16. (Yantai Rongchang, China); S-3APG, (Boston Children's Hospital. USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany), AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEOF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds of the present invention can be modified to target specific receptors or cancer cells or can be modified so that they can survive various in vivo environments. As examples, the compounds of the present invention can be modified so that they are combined with dendrimers or other cyclic sugars to form carboxylate dendrimers or other sugars. They may be combined with steroids such as estrogen to form carboxylate steroids like carboxylate estrogen. If the compounds of the present invention contain carboxylate functionalities, the carboxylate functionalities on these compounds may be modified so that they contain folic acid. Those of skill in the art will recognize that there are other modifications that can be made to the compounds of the present invention so that they can target specific receptors, cells or provide stability to the compounds. It is contemplated that the compounds of the present invention can have modifications made that are covalent modifications, ionic modifications, modified so that they chelate to other compounds, or other undergo some other type of interaction that allows the compounds of the present invention to suit their use (such as hydrophobic or Van der Waals type interactions).

In a further variation, the compounds of the present invention can be used against solid tumors, cell lines, and cell line tissue that demonstrate upregulated nucleotide excision repair and other upregulated resistance mechanisms. Thus, in an embodiment, the present invention discloses methods of treating cancer in an individual in need thereof by the use of a compound of Formulas I and/or II.

The Platinum-based and Gold-based compounds of the present invention may also be used against genitourinal (bladder, ovaries, testes) cancers and carcinomas of the head and neck, as well as colon cancers. Although the compounds of the present invention may also show promise against these various cancers and carcinomas, the compounds of the present invention show an altered spectrum of activity compared to previous drugs used against these various cancers and carcinomas, the compounds of the present invention also show excellent activity in cancers insensitive to the clinical platinums of the prior art.

In a variation, the compounds of the present invention can be used for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

In a variation, the compounds of the present invention can be used in the treatment of non-small cell lung cancer, pancreatic cancer, breast cancer, and ovarian cancer. Alternatively, the compounds of the present invention can be used in the treatment of non-small cell lung cancer, pancreatic, and ovarian cancer.

In an embodiment, the compounds of the present invention also have potential applications as antiviral and anti-Alzheimer's drugs.

Thus, it is contemplated that the compounds, compositions and methods of the present invention may be useful for first- and/or second-line treatment option for cancers that are inherently resistant, or, have become resistant to clinical therapies, especially classical platinum drugs. The compounds of the present invention may provide an avenue to solve the urgent need for mechanistically novel drugs for the life-prolonging/curative treatment of NSCLC.

It is contemplated and therefore within the scope of the present invention that any feature that is disclosed in the present invention can be combined with any other feature in the present invention. For example, if a variable is described with reference to formula I, it should be recognized that it is contemplated and therefore within the scope of the present invention that the defined variable can also be used with Formula II. It is also contemplated that minor modifications can be made to the present invention.

The following references are incorporated by reference in their entireties.

[1] T. Yoshida, G. Zhang, E. B. Haura, Biochem. Pharmacol. 2010, 80, 613-623.

[2] a) J. G. Paez, P. A. Janne, J. C. Lee, S. Tracy, H. Greulich, S. Gabriel, P. Herman, F. J. Kaye, N. Lindeman, T. J. Boggon, K. Naoki, H. Sasaki, Y. Fujii, M. J. Eck, W. R. Sellers, B. E. Johnson, M. Meyerson, Science 2004, 304, 1497-1500; b) S. V. Sharma, D. W. Bell, J. Settleman, D. A. Haber, Nat. Rev. Cancer 2007, 7, 169-181.

[3] W. Pao, V. Miller, M. Zakowski, J. Doherty, K. Politi, I. Sarkaria, B. Singh, R. Heelan, V. Rusch, L. Fulton, E. Mardis, D. Kupfer, R. Wilson, M. Kris, H. Varmus, Proc. Natl. Acad. Sci. USA 2004, 101, 13306-13311.

[4] C. H. Yun, K. E. Mengwasser, A. V. Toms, M. S. Woo, H. Greulich, K. K. Wong, M. Meyerson, M. J. Eck, Proc. Natl. Acad. Sci. USA 2008, 105, 2070-2075.

[5] Q. Liu, Y. Sabnis, Z. Zhao, T. Zhang, S. J. Buhrlage. L. H. Jones, N. S. Gray, Chem. Biol. 2013, 20, 146-159.

[6] V. Hirsh, Future Oncol. 2011, 7, 817-825.

[7] A. Kumar, E. T. Petri, B. Halmos. T. J. Boggon, J. Clin. Oncol. 2008, 26, 1742-1751.

[8] S. J. Berners-Price, A. Filipovska, Metallomics 2011, 3, 863-873.

[9] E. Erdogan, T. Lamark, M. Stallings-Mann, J. Lee, M. Pellecchia, E. A. Thompson, T. Johansen, A. P. Fields, J. Biol. Chem. 2006, 281, 28450-28459.

[10] J. Zhang, P. L. Yang, N. S. Gray, Nat. Rev. Cancer 2009, 9, 28-39.

[11] a) L. C. Eiter, N. W. Hall, C. S. Day, G. Saluta, G. L. Kucera, U. Bierbach, J. Med. Chem. 2009, 52, 6519-6522; b) K. Yan, C. N. Lok, K. Bierla, C. M. Che, Chem. Commun. 2010, 46, 7691-7693; c) S. Ahmad, A. A. Isab, J. Inorg. Biochem. 2002, 88, 44-52.

[12] M. Y. Cha, K. O. Lee, J. W. Kim, C. G. Lee, J. Y. Song, Y. H. Kim, G. S. Lee, S. B. Park, M. S. Kim, J. Med. Chem. 2009, 52, 6880-6888.

[13] R. Uson, A. Laguna, M. Laguna, D. A. Briggs, H. H. Murray, J. P. Fackler, Inorg. Synth. 1989, 26, 85-91.

[14] C. Levallet, J. Lerpiniere, S. Y. Ko, Tetrahedron 1997, 53, 5291-5304.

[15] F. G. Mann, A. F. Wells, D. Purdie, J. Chem. Soc. 1937, 1828.

[16] L. A. Marcaurelle, E. Comer, S. Dandapani, J. R. Duvall, B. Gerard, S. Kesavan, M. D. T. Lee, H. Liu, J. T. Lowe, J. C. Marie, C. A. Mulrooney, B. A. Pandya, A. Rowley, T. D. Ryba, B. C. Suh, J. Wei, D. W. Young, L. B. Akella, N. T. Ross, Y. L. Zhang, D. M. Fass, S. A. Reis, W. N. Zhao, S. J. Haggarty, M. Palmer, M. A. Foley, J. Am. Chem. Soc. 2010, 132, 16962-16976.

[17] M. M. Hamed, D. A. Abou El Ella, A. B. Keeton, G. A. Piazza, A. H. Abadi, R. W. Hartmann, M. Engel, ChemMedChem 2013, 8, 1495-1504.

[18] K. S. Gajiwala, J. Feng, R. Ferre, K. Ryan, O. Brodsky, S. Weinrich, J. C. Kath, A. Stewart, Structure 2013, 21, 209-219.

[19] A. A. Isab, M. Fettouhi, S. Ahmad, L. N. Ouahab, Polyhedron 2003, 22, 1349-1354.

[20] V. Gandin, A. P. Fernandes, M. P. Rigobello, B. Dani, F. Sorrentino, F. Tisato, M. Bjornstedt, A. Bindoli, A. Sturaro, R. Rella, C. Marzano, Biochem. Pharmacol. 2010, 79, 90-101.

[21] a) R. Sordella, D. W. Bell, D. A. Haber, J. Settleman, Science 2004, 305, 1163-1167; b) J. Deng, T. Shimamura, S. Perera, N. E. Carlson, D. Cai, G. L Shapiro, K. K. Wong, A. Letai, Cancer. Res. 2007, 67, 11867-11875.

[22] a) M. J. Frisch, G. W. Trucks, H. B. Schlegel, G. E. Scuseria, M. A. Robb, J. R. Cheeseman, J. A. Montgomery, T. Vreven, K. N. Kudin, J. C. Burant. J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui. A. G. Baboul, S. Clifford, J. Cioslowski, B. B. Stefanov, G. Liu, A. Liashenko, P. Piskorz, I. Komaromi, R. L. Martin, D. J. Fox, T. Keith, A. Laham, C. Y. Peng, A. Nanayakkara, M. Challacombe, P. M. W. Gill, B. Johnson, W. Chen, M. W. Wong, C. Gonzalez, J. A. Pople, Gaussian 03, Revision D.02, 2003; b) T. H. J. Dunning, P. J. Hay, Mod. Theor. Chem. 1977, 3, 1-27.

[23] O. Trott, A. J. Olson, J. Comput. Chem. 2010, 31, 455-461.

We claim:

1. A compound, pharmaceutically acceptable salt, or solvate of Formula I or Ia:

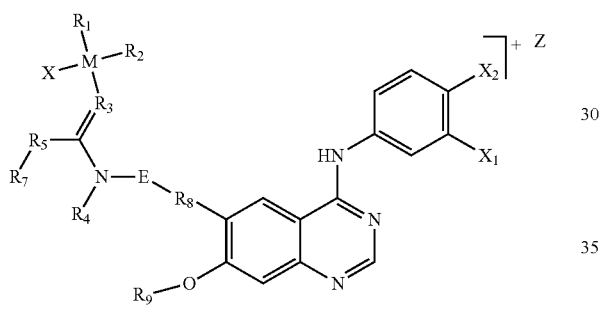

FORMULA I

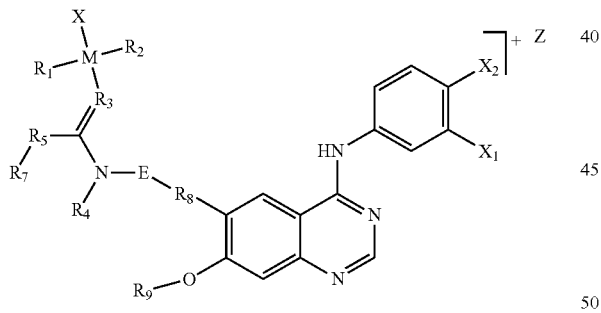

FORMULA Ia wherein X is halide, OH⁻, H$_2$O, —OC(O)R$_9$, —P((—CH$_2$)qCH$_3$)$_3$, nitrate, sulfate or a carbene of structure

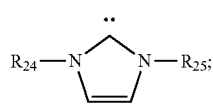

wherein q is 0, 1, 2, or 3;

X$_1$ and X$_2$ are independently halo, C$_{1-6}$alkoxy, C$_{1-6}$alkyl, C$_{2-6}$alkynyl, nitro, amino, —NHC(O)(R$_{10}$), —NHC(O)O(R$_{10}$), —C(O)NHR$_{10}$, or —OC(O)NHR$_{10}$;

M is Au or Pt and if M is Au, R$_1$ and R$_2$ are not present; R$_1$ and R$_2$ are amino, ammonia or pyridine groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

a

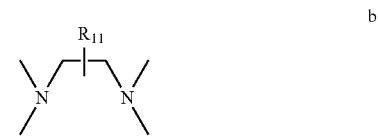

b

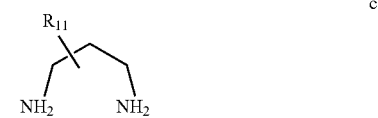

c

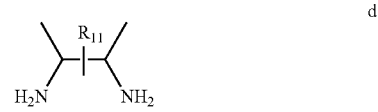

d

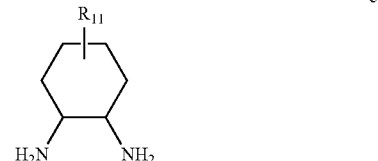

e

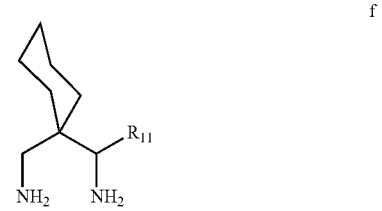

f

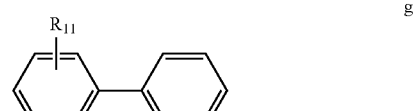

g

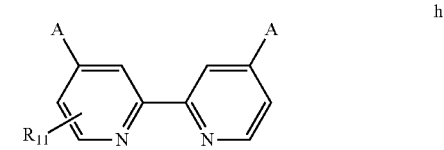

h wherein A is H, —CH$_3$, —OCH$_3$, CF$_3$ or NO$_2$;

R$_3$ is —N(R$_{26}$)— or S; wherein R$_{26}$ is hydrogen or C$_1$-C$_6$alkyl;

R$_4$ is hydrogen, C$_{1-6}$ alkyl, or CH$_2$—R$_{12}$;

E is —(CH$_2$)$_q$—;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

$R_{19}$ is hydrogen or $C_{1-6}$ alkyl;

$R_{20}$ is hydrogen, $C_{1-6}$ alkyl;

$R_8$ is —$NR_{13}$—, —C(O) $NR_{13}$—, —$NR_{13}$C(O)—, —O—, —S—, —OC(O)—, and —C(O)O—

$R_{13}$ is —H or —$C_{1-6}$alkyl;

$R_9$ is hydrogen, $C_{1-6}$ alkyl, phenyl, naphthyl, $C_{3-6}$ cycloalkyl, norbornyl, adamantyl, a natural or unnatural amino acid or a peptide;

$R_{11}$ and $R_{12}$ are independently hydrogen, hydroxyl, $C_{1-6}$ alkyl, —$OCH_3$, —$CF_3$, $NO_2$;

$R_{24}$ and $R_{25}$ are independently hydrogen or $C_{1-4}$alkyl; and

Z is independently one or more halide or nitro, or one or more counterions sufficient to balance the charge of the compound.

2. The compound, pharmaceutically acceptable salt, or solvate of claim 1 wherein $X_1$ is F or Cl and $X_2$ is F or Cl.

3. The compound, pharmaceutically acceptable salt, or solvate of claim 1, wherein $X_2$ is F and $X_1$ is Cl.

4. The compound, pharmaceutically acceptable salt, or solvate of claim 1 wherein M is Au and X is —P(—$CH_2$—$CH_3$)$_3$.

5. The compound, pharmaceutically acceptable salt, or solvate of claim 1 wherein $R_3$ is —NH or S.

6. The compound, pharmaceutically acceptable salt, or solvate of claim 1 wherein $R_5$ and $R_7$ together are ethyl or —$NHCH_3$.

7. The compound, pharmaceutically acceptable salt, or solvate of claim 1 wherein $R_4$ is H or $CH_3$.

8. The compound, pharmaceutically acceptable salt, or solvate of claim 1 wherein $R_{13}$ is H or $CH_3$.

9. The compound, pharmaceutically acceptable salt, or solvate of claim 1 wherein $R_9$ is ethyl.

10. The compound, pharmaceutically acceptable salt, or solvate of claim 1 wherein $X_1$ is $C_1$ and $X_2$ is F, wherein $R_3$ is —NH or S, wherein $R_5$ and $R_7$ together are ethyl or —$NHCH_3$, wherein E is methylene, wherein $R_4$ is H or $CH_3$, wherein $R_{13}$ is H or $CH_3$, and wherein $R_9$ is ethyl.

11. A pharmaceutical composition comprising compound, pharmaceutically acceptable salt, or solvate of Formula I or Formula Ia:

FORMULA I

FORMULA Ia wherein X is halide, OH, $H_2O$, —OC(O)$R_9$, —P((—$CH_2$)q$CH_3$)$_3$, nitrate, sulfate or a carbene of structure wherein q is 0, 1, 2, or 3;

$X_1$ and $X_2$ are independently halo, $C_{1-6}$alkoxy, $C_{1-6}$alkyl, $C_{2-6}$alkynyl, nitro, amino, —NHC(O)($R_{10}$), —NHC(O)O($R_{10}$), —C(O)NH$R_{10}$, or —OC(O)NH$R_{10}$;

M is Au or Pt and if M is Au, $R_1$ and $R_2$ are not present;

$R_1$ and $R_2$ are amino, ammonia or pyridine groups or together with the platinum atom to which they are attached, $R_1$ and $R_2$ form the ring —$NH_2$—$(CH_2)_v$—$NH_2$— wherein v is 1, 2, 3, or 4 or $R_1$ and $R_2$ together can be any of the following groups a-h;

-continued

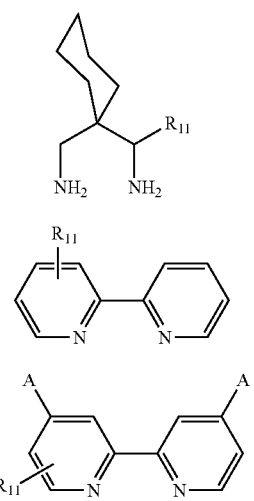

f g h wherein A is H, —CH$_3$, —OCH$_3$, CF$_3$ or NO$_2$;

R$_3$ is —N(R$_{26}$)— or S; wherein R$_{26}$ is hydrogen or C$_1$-C$_6$alkyl;

R$_4$ is hydrogen, C$_{1-6}$ alkyl, or CH$_2$—R$_{12}$;

E is —(CH$_2$)$_q$—;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_8$ is —NR$_{13}$—, —C(O) NR$_{13}$—, —NR$_{13}$C(O)—, —O—, —S—, —OC(O)—, and —C(O)O—

R$_{13}$ is —H or —C$_{1-6}$alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

R$_{11}$ and R$_{12}$ are independently hydrogen, hydroxyl, C$_{1-6}$ alkyl, —OCH$_3$, —CF$_3$, NO$_2$;

R$_{24}$ and R$_{25}$ are independently hydrogen or C$_{1-4}$alkyl; and

Z is independently one or more halide or nitro, or one or more counterions sufficient to balance the charge of the compound and one or more pharmaceutically acceptable diluents, excipients, or carriers.

12. The composition of claim 11, wherein X$_1$ is F or C$_1$ and X$_2$ is F or Cl.

13. The composition of claim 11, wherein X$_2$ is F and X$_1$ is Cl.

14. The composition of claim 11, wherein M is Au and X is —P(—CH$_2$—CH$_3$)$_3$.

15. The composition of claim 11, wherein R$_3$ is —NH or S.

16. The composition of claim 11, wherein R$_5$ and R$_7$ together are ethyl or —NHCH$_3$.

17. The composition of claim 11, wherein R$_4$ is H or CH$_3$ and wherein R$_{13}$ is H or CH$_3$.

18. The composition of claim 11, wherein R$_9$ is ethyl.

19. A method of treating cancer comprising administering to an individual in need thereof a compound, a pharmaceutically acceptable salt, or a solvate of Formula I or Formula Ia:

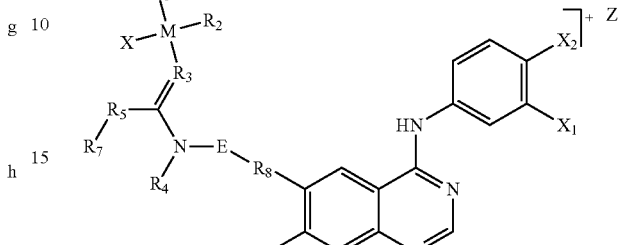

FORMULA I

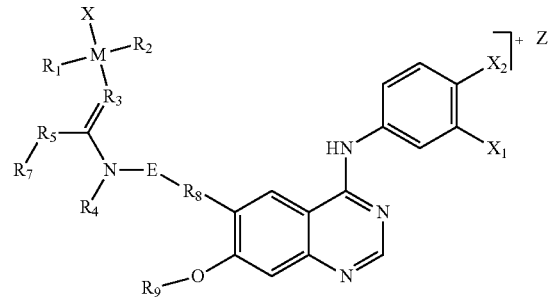

FORMULA Ia wherein X is halide, OH, H$_2$O, —OC(O)R$_9$, —P((—CH$_2$)qCH$_3$)$_3$, nitrate, sulfate or a carbene of structure

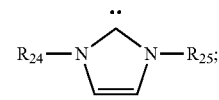

wherein q is 0, 1, 2, or 3;

X$_1$ and X$_2$ are independently halo, C$_{1-6}$alkoxy, C$_{1-6}$alkyl, C$_{2-6}$alkynyl, nitro, amino, —NHC(O)(R$_{10}$), —NHC(O)O(R$_{10}$), —C(O)NHR$_{10}$, or —OC(O)NHR$_{10}$;

M is Au or Pt and if M is Au, R$_1$ and R$_2$ are not present;

R$_1$ and R$_2$ are amino, ammonia or pyridine groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

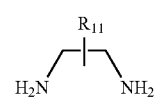

a

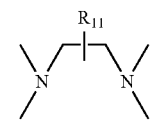

b

-continued c 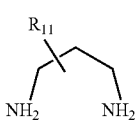

d 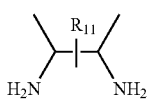

e 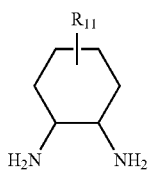

f 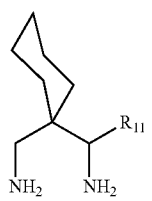

g 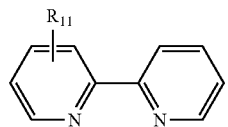

h 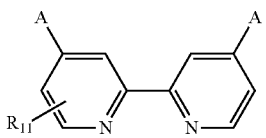

wherein A is H, —CH$_3$, —OCH$_3$, CF$_3$ or NO$_2$;
R$_3$ is —N(R$_{26}$)— or S; wherein R$_{26}$ is hydrogen or C$_1$-C$_6$alkyl;

R$_4$ is hydrogen, C$_{1-6}$ alkyl, or CH$_2$—R$_{12}$;
E is —(CH$_2$)$_q$—;
R$_5$ is a direct bond, —NH— or C$_1$-C$_6$alkylene;
or R$_5$ and X together with the atoms to which they are attached form a 6- or 7-membered ring, wherein said 6- or 7-membered ring contains a linking group —C(O)O— or —OC(O)—;
R$_7$ is hydrogen, methyl, —CH(R$_{17}$)(R$_{18}$), —C(O)O—R$_{18}$, or —OC(O)—R$_{18}$; wherein
R$_{17}$ is hydrogen or C$_{1-6}$ alkyl;
R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;
R$_{19}$ is hydrogen or C$_{1-6}$ alkyl;
R$_{20}$ is hydrogen, C$_{1-6}$ alkyl;
R$_8$ is —NR$_{13}$—, —C(O) NR$_{13}$—, —NR$_{13}$C(O)—, —O—, —S—, —OC(O)—, and —C(O)O—
R$_{13}$ is —H or —C$_{1-6}$alkyl;
R$_9$ is hydrogen, C$_{1-6}$ alkyl, phenyl, naphthyl, C$_{3-6}$ cycloalkyl, norbornyl, adamantyl, a natural or unnatural amino acid or a peptide;
R$_{11}$ and R$_{12}$ are independently hydrogen, hydroxyl, C$_{1-6}$ alkyl, —OCH$_3$, —CF$_3$, NO$_2$;
R$_{24}$ and R$_{25}$ are independently hydrogen or C$_{1-4}$alkyl; and
Z is independently one or more halide or nitro, or one or more counterions sufficient to balance the charge of the compound;
wherein said cancer is selected from the group consisting of non-small cell lung cancer, small cell lung cancer, colorectal, pancreatic cancer, brains stem glioma, cancer of the head or neck, and Her2-positive breast cancer.

20. The method of claim 19, wherein the cancer is non-small cell lung cancer.

21. A method of inhibiting EGFR expressed on a cell comprising contacting a compound of claim 1 with a cell having overexpressed or mutated EGFR.

22. The method of claim 19, wherein the cancer is selected from the group consisting of non-small cell lung cancer, colorectal, pancreatic cancer, brains stem glioma, cancer of the head or neck, and Her2-positive breast cancer.

* * * * *